US012649732B2

(12) United States Patent
Tom et al.

(10) Patent No.: US 12,649,732 B2
(45) Date of Patent: Jun. 9, 2026

(54) POLYMORPHS OF (R)-N-(5-(5-ISOPROPYL-1,2,4-OXADIAZOL-3-YL)-2,3-DIHYDRO-1H-INDEN-1-YL)-2-METHYL-2H-TETRAZOLE-5-CARBOXAMIDE

(71) Applicant: Cytokinetics, Inc., South San Francisco, CA (US)

(72) Inventors: Norma Tom, Belmont, CA (US); Denise Andersen, Montara, CA (US)

(73) Assignee: CYTOKINETICS, INC., South San Francisco, CA (US)

( * ) Notice: Subject to any disclaimer, the term of this patent is extended or adjusted under 35 U.S.C. 154(b) by 1180 days.

(21) Appl. No.: 17/627,590

(22) PCT Filed: Jul. 16, 2020

(86) PCT No.: PCT/US2020/042390

§ 371 (c)(1),
(2) Date: Jan. 14, 2022

(87) PCT Pub. No.: WO2021/011809

PCT Pub. Date: Jan. 21, 2021

(65) Prior Publication Data

US 2022/0274969 A1 Sep. 1, 2022

Related U.S. Application Data

(60) Provisional application No. 62/875,355, filed on Jul. 17, 2019.

(51) Int. Cl.
*C07D 413/12* (2006.01)

(52) U.S. Cl.
CPC ........ *C07D 413/12* (2013.01); *C07B 2200/13* (2013.01)

(58) Field of Classification Search
CPC .......................... C07D 413/12; C07B 2200/13
See application file for complete search history.

(56) References Cited

U.S. PATENT DOCUMENTS

| | | | | |
|---|---|---|---|---|
| 8,802,735 | B2 | 8/2014 | Hauck | |
| 10,836,755 | B2 * | 11/2020 | Chuang | C07D 413/04 |
| 11,472,796 | B2 | 10/2022 | Chuang et al. | |
| 11,932,631 | B2 | 3/2024 | Andersen | |
| 12,065,436 | B2 | 8/2024 | Chuang | |
| 2006/0173183 | A1 | 8/2006 | Powers | |
| 2007/0049603 | A1 | 3/2007 | Miknis | |
| 2009/0192168 | A1 | 7/2009 | Muci et al. | |
| 2013/0186801 | A1 | 7/2013 | Verwijs | |
| 2014/0378491 | A1 | 12/2014 | Oslob | |
| 2016/0016914 | A1 | 1/2016 | Ladziata | |
| 2017/0087180 | A1 | 3/2017 | Giordano et al. | |
| 2017/0096435 | A1 | 4/2017 | Tebbe | |
| 2019/0256504 | A1 * | 8/2019 | Chuang | C07D 413/12 |
| 2021/0253563 | A1 | 8/2021 | Morgan et al. | |
| 2021/0276991 | A1 | 9/2021 | Morgan et al. | |
| 2022/0265612 | A1 | 8/2022 | Qiao | |
| 2022/0315571 | A1 | 10/2022 | Tom et al. | |
| 2023/0058927 | A1 | 2/2023 | Malik et al. | |
| 2024/0091203 | A1 | 3/2024 | Heitner | |
| 2024/0115554 | A1 | 4/2024 | Malik | |
| 2025/0059173 | A1 | 2/2025 | Chuang et al. | |
| 2025/0177357 | A1 | 6/2025 | Malik et al. | |

FOREIGN PATENT DOCUMENTS

| | | | |
|---|---|---|---|
| CA | 2570999 | A1 | 1/2006 |
| CL | 2020001871 | A1 | 10/2020 |
| CL | 2022001091 | A1 | 1/2023 |
| CN | 102596184 | A | 7/2012 |
| CN | 111757875 | A | 10/2020 |
| EP | 3156049 | A1 | 4/2017 |
| EP | 3999180 | B1 | 5/2024 |
| EP | 3999181 | B1 | 5/2024 |
| IL | 276094 | A | 8/2020 |
| IN | 202017035146 | A | 9/2020 |
| JP | 2021511331 | A | 5/2021 |
| MX | 2020007532 | A | 9/2020 |
| RU | 2410384 | C2 | 1/2011 |
| SG | 11202006296 | Y | 8/2020 |
| WO | 2004064730 | A2 | 8/2004 |
| WO | 2006009726 | A2 | 1/2006 |
| WO | 2007078815 | A2 | 7/2007 |
| WO | 2011005832 | A1 | 1/2011 |
| WO | 2012101011 | A2 | 8/2012 |
| WO | 2014205234 | A1 | 12/2014 |
| WO | 2019006235 | A1 | 1/2019 |
| WO | 2019055590 | A1 | 3/2019 |
| WO | 2019144041 | A1 | 7/2019 |
| WO | 2020005887 | A1 | 1/2020 |
| WO | 2020005888 | A1 | 1/2020 |
| WO | 2021011807 | A1 | 1/2021 |

(Continued)

OTHER PUBLICATIONS

Bauer, J. et al. Ritonavir: An Extraordinary Example of Conformational Polymorphism. Pharm. Res. 2001, 18, 859-866. (Year: 2001).*
Non-final rejection notification date Nov. 20, 2019, for U.S. Appl. No. 16/252,483, filed Jan. 18, 2019, 8 pages. (Year: 2019).*
Applicant Remarks dated Feb. 20, 2020, for U.S. Appl. No. 16/252,483, filed Jan. 18, 2019, 8 pages. (Year: 2020).*
Brittain, H.G. Polymorphism in Pharmaceutical Solids, 2nd ed.; Drugs and the pharmaceutical sciences, 2009. p. 333-338 provided. (Year: 2009).*
Lee, E. H. A practical guide to pharmaceutical polymorph screening & selection. Asian J. Pharm. Sci. 2014, 9, 163-175. (Year: 2014).*
Berge, S.M. et al. (Jan. 1977). "Pharmaceuticals Salts," J. Pharmaceutical Sciences 66(1):1-19.

(Continued)

*Primary Examiner* — Jeffrey H Murray
*Assistant Examiner* — Kristen W Romero
(74) *Attorney, Agent, or Firm* — MORRISON & FOERSTER LLP

(57) ABSTRACT

Provided herein are polymorphs of (R)—N-(5-(5-isopropyl-1,2,4-oxadiazol-3-yl)-2,3-dihydro-1H-inden-1-yl)-2-methyl-2H-tetrazole-5-carboxamide, compositions thereof, methods of preparation thereof, and methods of their uses.

12 Claims, 11 Drawing Sheets

(56) References Cited

FOREIGN PATENT DOCUMENTS

| | | | |
|---|---|---|---|
| WO | 2021011808 | A1 | 1/2021 |
| WO | 2021011809 | A1 | 1/2021 |
| WO | 2024134498 | A1 | 6/2024 |
| WO | 2024179422 | A1 | 9/2024 |
| WO | 2024182469 | A1 | 9/2024 |
| WO | 2025/220034 | A1 | 10/2025 |

OTHER PUBLICATIONS

Guazzi, M. et al. (Sep. 26, 2017). "Cardiopulmonary Exercise Testing: What Is its Value?," J. Am. Coll. Cardiol. 70(13):1618-1636.

International Preliminary Report on Patentability mailed Jan. 27, 2022, for Patent Application No. PCT/US2020/042387, filed Jul. 16, 2020, 8 pages.

International Preliminary Report on Patentability mailed Jan. 27, 2022, for Patent Application No. PCT/US2020/042389, filed Jul. 16, 2020, 8 pages.

International Preliminary Report on Patentability mailed Jan. 27, 2022, for Patent Application No. PCT/US2020/042390, filed Jul. 16, 2020, 8 pages.

International Search Report and Written Opinion of the International Searching Authority mailed Nov. 10, 2020, for PCT Patent Application No. PCT/US2020/042387, filed Jul. 16, 2020, 13 pages.

International Search Report and Written Opinion of the International Searching Authority mailed Nov. 5, 2020, for PCT Patent Application No. PCT/US2020/042389, filed Jul. 16, 2020, 13 pages.

International Search Report and Written Opinion of the International Searching Authority mailed Nov. 6, 2020, for PCT Patent Application No. PCT/US2020/042390, filed Jul. 16, 2020, 14 pages.

Malhotra, R. et al. (Aug. 2016, e-pub. Jun. 8, 2016). "Cardiopulmonary Exercise Testing in Heart Failure," JACC Heart Fail 4(8):607-616.

Philipson, D. J. et al. (2017, e-pub. Aug. 31, 2017). "Emerging Pharmacologic and Structural Therapies For Hypertrophic Cardiomyopathy," Heart Fail Rev. 22(6):879-888.

Rowin, E.J. et al. (Nov. 2017). "Role of Exercise Testing in Hypertrophic Cardiomyopathy," JACC: Cariovasc Imaging. 10(11):1374-1386.

Taub, P.R. et al. (Oct. 1, 2013). "Perturbations in Skeletal Muscle Sarcomere Structure in Patients with Heart Failure and Type 2 Diabetes: Restorative Effects of (-)-epicatechin-rich Cocoa," Clinical Science 125(8):383-389.

U.S. Appl. No. 17,823,910, filed on Aug. 31, 2022, for Chihyuan et al. (A U.S. Patent Application is not submitted herewith pursuant to the waiver of 37 C.F.R § 1.98(a)(2)(iii) issued by the Office on Sep. 21, 2004.).

Bernstein, J. (2002). "Polymorphism In Molecular Crystals," First ed. Oxford University Press Inc.: New York, NY. (Table of Contents Only.).

Blagova O.V. et al. (2017). "Classification Of Non-Coronary Heart Diseases: Our View On The Problem," Russian Journal of Cardiology (2)142:7-21. English Abstract.

Brief Communication—Opposition Proceedings dated Jun. 30, 2025, for European Patent Application No. 20753562.6, Proprietor's Response To Notice of Opposition European Patent 3999180B1, 20 pages.

Caira, M.R. (1998). "Crystalline Polymorphism of Organic Compounds," in Design of Organic Solids, Topics in Current Chemistry 198:163-208.

CAS No. 7087-68-5 (Jan. 27, 2025). "N,N-Diisopropylethylamine," Chemical Book, located at https://www.chemicalbook.com/ChemicalProductProperty_EN_CB4854144.htm, last visited on Mar. 3, 2025, 2 pages.

Certified U.S. Appl. No. 62/875,350, filed Jul. 17, 2019, for Norma TOM, 94 pages.

Hartman, J.J. et al. (Aug. 2024, e-pub. Jul. 23, 2024). "Aficamten Is A Small-Molecule Cardiac Myosin Inhibitor Designed To Treat Hypertrophic Cardiomyopathy," Nature Cardiovascular Research (3): 1003-1016.

King, R.E. et al. (1985). "Oral Solid Dosage Forms," Chapter 90 in Remington's Pharmaceutical Sciences, 17th ed. pp. 1603-1632.

Kümmerer, K. (2010). "Pharmaceuticals in the Environment," Annual Review of Environment and Resources 35:57-75.

Moore, J.R. et al. (Jul. 20, 2012). "Understanding Cardiomyopathy Phenotypes Based on the Functional Impact of Mutations in the Myosin Motor," Circulation Research 111:375-385.

Newman, A. (Oct. 30, 2012). "Specialized Solid Form Screening Techniques," Organic Process Research & Development 13(3):457-471.

Noriaki, H. (Jul. 25, 2008). "Pharmaceutical Crystallization Methods," Chapter 4 in Handbook of Organic Compound Crystal Preparation: Principles and Know-how, Maruzen Publishing: Tokyo, Japan, pp. 57-79, 14 pages. (English Machine Translation of Abstract Only.).

Notice of Opposition for European Patent Application No. 20753562.6 communicated to Patentee on Feb. 13, 2025, filed by opponent on Feb. 7, 2025, 10 pages.

Pifferi, G. et al. (2003). "The Safety of Pharmaceutical Excipients," IL Ffarmaco 58:541-550.

Rodriguez-Spong, B. et al. (2004). "General principles of Pharmaceutical Solid Polymorphism: A Supramolecular Perspective," Advanced Drug Delivery Review 56:241-274. (Abstract).

Sarma, B. et al. (Jan. 31, 2011). "Solid Formation of Pharmaceuticals: Polymorphs, Salt and Cocrystals," Korean J. Chem. Eng. 28(2):315-322.

Siew, A. (Apr. 2017). "Designing Optimized Formulations," Pharmaceutical Technology 41(4): 16-21.

Sommese, R.F. et al. (Jul. 30, 2013). "Molecular Consequences of the R453C Hypertrophic Cardiomyopathy Mutation on Human B-cardiac Myosin Motor Function," PNAS 110(31):12607-12612.

Third Party Observation for Application No. EP20200753562 dated Jan. 23, 2025, for EP Patent Publication No. EP3999180, 2 pages.

* cited by examiner

POLYMORPHS OF (R)-N-(5-(5-ISOPROPYL-1,2,4-OXADIAZOL-3-YL)-2,3-DIHYDRO-1H-INDEN-1-YL)-2-METHYL-2H-TETRAZOLE-5-CARBOXAMIDE

CROSS REFERENCE TO RELATED APPLICATIONS

This application is a national stage application under 35 U.S.C. § 371 of International Application No. PCT/US2020/042390, filed Jul. 16, 2020, which claims priority to and the benefit of U.S. Provisional Application No. 62/875,355, filed on Jul. 17, 2019, the entire disclosures of which are incorporated herein by reference in their entirety.

FIELD

Provided herein are polymorphs of (R)—N-(5-(5-isopropyl-1,2,4-oxadiazol-3-yl)-2,3-dihydro-1H-inden-1-yl)-2-methyl-2H-tetrazole-5-carboxamide, compositions thereof, methods of preparation thereof, and methods of their uses.

BACKGROUND

The cardiac sarcomere is composed of a network of contractile and structural proteins that regulate cardiac muscle function. The components of the cardiac sarcomere present targets for the treatment of various cardiac diseases and conditions, for example by increasing contractility or facilitating complete relaxation to modulate systolic and diastolic function, respectively. The force and speed of cardiac muscle contraction is a major determinant of organ function and is modulated by the cyclical interactions of actin and myosin. Regulation of actin and myosin binding is determined by a network of myofilament regulatory proteins and the level of intracellular $Ca^{2+}$. The troponin complex and tropomyosin are thin filament proteins which govern the availability of actin binding sites, and the essential and regulatory light chains, and myosin binding protein C modulate the position and mechanical properties of myosin.

Abnormalities in the cardiac sarcomere have been identified as the driving cause for a variety of cardiac diseases and conditions, such as hypertrophic cardiomyopathy (HCM) and heart failure with preserved ejection fraction (HFpEF). Mutations in the proteins of the sarcomere cause disease by rendering the cardiac muscle either ‘hyper’ or ‘hypo’ contractile. Modulators of the cardiac sarcomere can be used to rebalance contractility and stop or reverse the course of disease.

Current agents that target the cardiac sarcomere, such as inotropes (drugs that increase the contractile ability of the heart) are poorly selective for cardiac tissue, which leads to recognized adverse effects that limit their use. These adverse effects include cell damage caused by an increased rate of energy expenditure, exacerbation of relaxation abnormalities, and potential arrhythmogenic side effects that may result from increased cytosolic Ca++ and cyclic AMP concentrations in the inotropically stimulated myocardium. Given the limitations of current agents, new approaches are needed to improve cardiac function in HCM and HFpEF.

There remains a great need for agents that exploit new mechanisms of action and may have better outcomes in terms of relief of symptoms, safety, and patient mortality, both short-term and long-term. New agents with an improved therapeutic index over current agents will provide a means to achieve these clinical outcomes. The selectivity of agents directed at the cardiac sarcomere (for example, by targeting cardiac myosin) has been identified as an important means to achieve this improved therapeutic index. (R)—N-(5-(5-isopropyl-1,2,4-oxadiazol-3-yl)-2,3-dihydro-1H-inden-1-yl)-2-methyl-2H-tetrazole-5-carboxamide is a selective allosteric inhibitor of cardiac myosin that have little to no effect on smooth muscle myosin. Benefits of this compound include a wider therapeutic index, less impact on cardiac relaxation, better pharmacokinetics, and better safety and therefore it provides a potential treatment for cardiac diseases and conditions.

To move a drug candidate such as (R)—N-(5-(5-isopropyl-1,2,4-oxadiazol-3-yl)-2,3-dihydro-1H-inden-1-yl)-2-methyl-2H-tetrazole-5-carboxamide to a viable pharmaceutical product, it can be important to understand whether the drug candidate has polymorph forms, as well as the relative stability and interconversions of these forms under conditions likely to be encountered upon large-scale production, transportation, storage and pre-usage preparation. The ability to control and produce a stable polymorph with a robust manufacturing process can be key for regulatory approval and marketing. Large scale production processes for high purity (R)—N-(5-(5-isopropyl-1,2,4-oxadiazol-3-yl)-2,3-dihydro-1H-inden-1-yl)-2-methyl-2H-tetrazole-5-carboxamide can be improved by use of particular polymorphic forms. Accordingly, there is a need for various new crystalline forms of (R)—N-(5-(5-isopropyl-1,2,4-oxadiazol-3-yl)-2,3-dihydro-1H-inden-1-yl)-2-methyl-2H-tetrazole-5-carboxamide with different chemical and physical stabilities, and formulations and uses of the same.

BRIEF SUMMARY

In one aspect, provided herein are polymorphs of (R)—N-(5-(5-isopropyl-1,2,4-oxadiazol-3-yl)-2,3-dihydro-1H-inden-1-yl)-2-methyl-2H-tetrazole-5-carboxamide.

In another aspect, provided herein are methods of preparing polymorphs of (R)—N-(5-(5-isopropyl-1,2,4-oxadiazol-3-yl)-2,3-dihydro-1H-inden-1-yl)-2-methyl-2H-tetrazole-5-carboxamide.

In another aspect, provided herein are compositions containing the polymorphs of (R)—N-(5-(5-isopropyl-1,2,4-oxadiazol-3-yl)-2,3-dihydro-1H-inden-1-yl)-2-methyl-2H-tetrazole-5-carboxamide as described herein.

In another aspect, provided herein are methods of treating heart disease in a subject in need thereof using polymorphs of (R)—N-(5-(5-isopropyl-1,2,4-oxadiazol-3-yl)-2,3-dihydro-1H-inden-1-yl)-2-methyl-2H-tetrazole-5-carboxamide.

DETAILED DESCRIPTION

Definitions

Figure 1A:
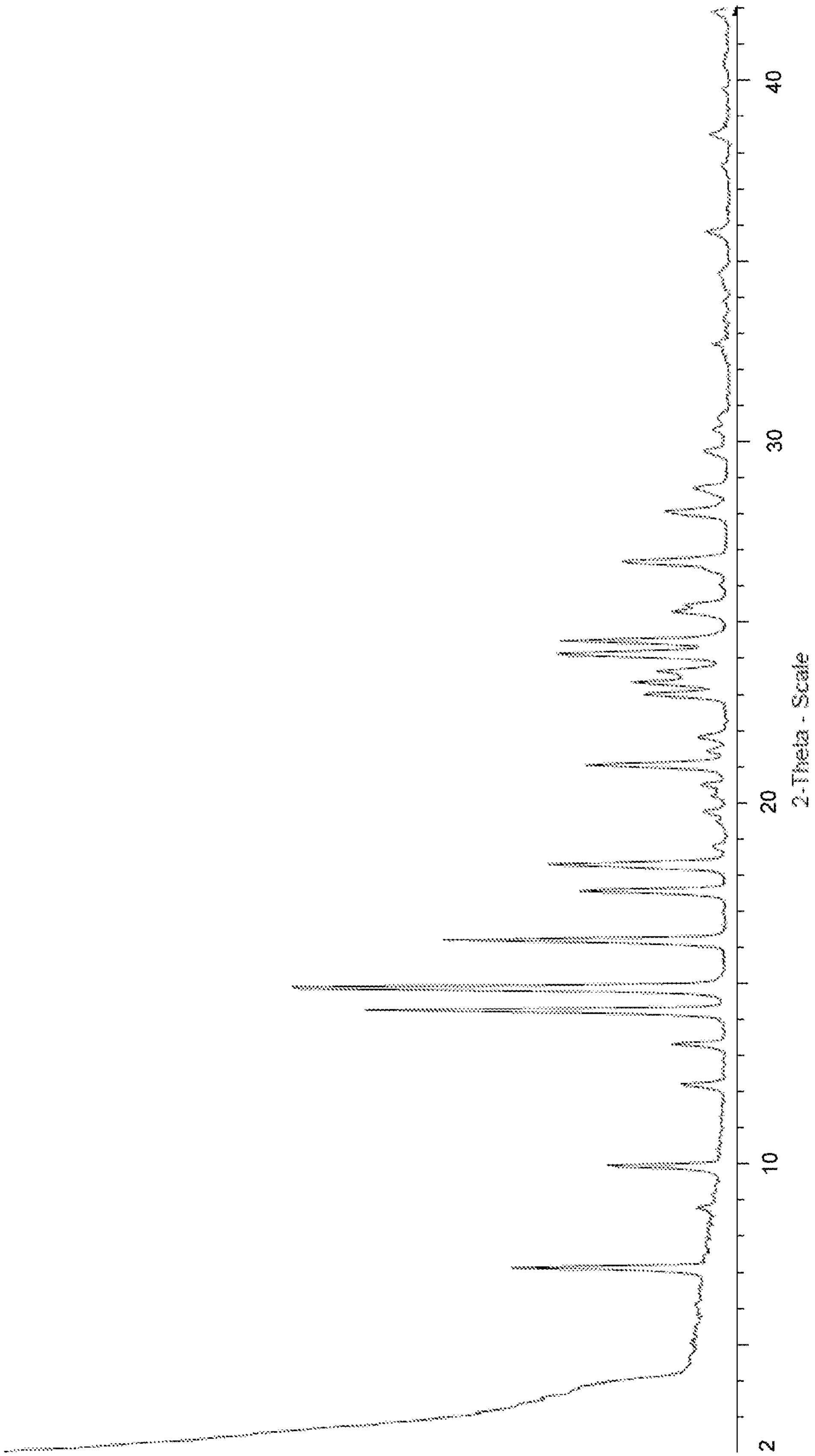
FIG. 1A shows an experimental X-ray powder diffraction (XRPD) pattern of polymorphic Form I of (R)—N-(5-(5-isopropyl-1,2,4-oxadiazol-3-yl)-2,3-dihydro-1H-inden-1-yl)-2-methyl-2H-tetrazole-5-carboxamide.

As used herein and in the appended claims, the singular forms "a", "an" and "the" include plural forms, unless the context clearly dictates otherwise.

As used herein, and unless otherwise specified, the terms "about" and "approximately," when used in connection with doses, amounts, or weight percent of ingredients of a composition or a dosage form, a mean dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, within 10%, within 5%, within 4%, within 3%, within 2%, within 1%, or within 0.5% of the specified dose, amount, or weight percent.

As used herein, the term "polymorph" or "polymorphic form" refers to a crystalline form of a compound. Different polymorphs may have different physical properties such as, for example, melting temperatures, heats of fusion, solubilities, dissolution rates, and/or vibrational spectra as a result of the arrangement or conformation of the molecules or ions in the crystal lattice. The differences in physical properties exhibited by polymorphs may affect pharmaceutical parameters, such as storage stability, compressibility, density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph), mechanical changes (e.g., tablets crumble on storage as a kinetically favored polymorph converts to thermodynamically more stable polymorph), or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of a crystalline form may be important in processing; for example, one polymorph might be more likely to form solvates or might be difficult to filter and wash free of impurities (e.g., particle shape and size distribution might be different between polymorphs).

As used herein, "therapeutically effective amount" indicates an amount that results in a desired pharmacological and/or physiological effect for the condition. The effect may be prophylactic in terms of completely or partially preventing a condition or symptom thereof and/or may be therapeutic in terms of a partial or complete cure for the condition and/or adverse effect attributable to the condition.

As used herein, the term "pharmaceutically acceptable carrier," and cognates thereof, refers to adjuvants, binders, diluents, etc. known to the skilled artisan that are suitable for administration to an individual (e.g., a mammal or non-mammal). Combinations of two or more carriers are also contemplated. The pharmaceutically acceptable carrier(s) and any additional components, as described herein, should be compatible for use in the intended route of administration (e.g., oral, parenteral) for a particular dosage form, as would be recognized by the skilled artisan.

The terms "treat," "treating," and "treatment" are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. Often, the beneficial effects that a subject derives from a therapeutic agent do not result in a complete cure of the disease, disorder or condition.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

As used herein, the term "substantially as shown in" when referring, for example, to an XRPD pattern, a DSC graph, a TGA graph, or a GVS graph, includes a pattern or graph that is not necessarily identical to those depicted herein, but that falls within the limits of experimental error or deviations when considered by one of ordinary skill in the art.

In some embodiments, the term "substantially pure" means that the polymorphic form contains about less than 30%, about less than 20%, about less than 15%, about less than 10%, about less than 5%, or about less than 1% by weight of impurities. In other embodiments, "substantially pure" refers to a substance free of impurities. Impurities may, for example, include by-products or left over reagents from chemical reactions, contaminants, degradation products, other polymorphic forms, water, and solvents.

As used herein, the term "substantially free of" means that the composition comprising the polymorphic form contains less than 50%, less than 40%, less than 30%, less than 20%, less than 15%, less than 10%, less than 5%, less than 4%, less than 3%, less than 2%, or less than 1% by weight of the indicated substance or substances.

Polymorphs

In one aspect, provided herein are polymorphs of (R)—N-(5-(5-isopropyl-1,2,4-oxadiazol-3-yl)-2,3-dihydro-1H-inden-1-yl)-2-methyl-2H-tetrazole-5-carboxamide, a compound having the structure shown below,

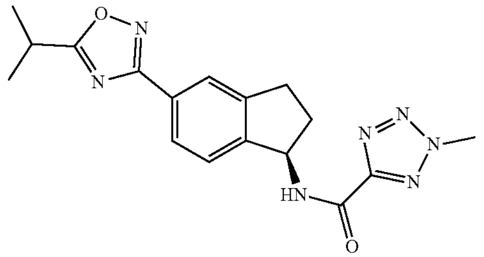 [SMILES: CC(C)c1nc(-c2ccc3c(c2)CC[C@H]3NC(=O)c2nnn(C)n2)no1]

The polymorphs may have properties such as bioavailability and stability under certain conditions that are suitable for medical or pharmaceutical uses.

A polymorph of (R)—N-(5-(5-isopropyl-1,2,4-oxadiazol-3-yl)-2,3-dihydro-1H-inden-1-yl)-2-methyl-2H-tetrazole-5-carboxamide may provide the advantages of bioavailability and stability and may be suitable for use as an active agent in a pharmaceutical composition. Variations in the crystal structure of a pharmaceutical drug substance may affect the dissolution rate (which may affect bioavailability, etc.), manufacturability (e.g., ease of handling, ease of purification, ability to consistently prepare doses of known strength, etc.) and stability (e.g., thermal stability, shelf life (including resistance to degradation), etc.) of a pharmaceutical drug product. Such variations may affect the methods of preparation or formulation of pharmaceutical compositions in different dosage or delivery forms, such as solid oral dosage forms including tablets and capsules. Compared to other forms such as non-crystalline or amorphous forms, polymorphs may provide desired or suitable hygroscopicity, particle size control, dissolution rate, solubility, purity, physical and chemical stability, manufacturability, yield, reproducibility, and/or process control. Thus, polymorphs of (R)—N-(5-(5-isopropyl-1,2,4-oxadiazol-3-yl)-2,3-dihydro-1H-inden-1-yl)-2-methyl-2H-tetrazole-5-carboxamide may provide advantages of improving the manufacturing process of an active agent or the stability or storability of a drug product form of the active agent, or having suitable bioavailability and/or stability as an active agent.

The use of certain conditions, such as the use of different solvents and/or temperatures, has been found to produce different polymorphs of (R)—N-(5-(5-isopropyl-1,2,4-oxadiazol-3-yl)-2,3-dihydro-1H-inden-1-yl)-2-methyl-2H-tetrazole-5-carboxamide, including polymorphic Forms I and II described herein, which may exhibit one or more favorable characteristics described herein. The processes for the preparation of the polymorphs described herein and characterization of these polymorphs are described in greater detail below.

Form I

In some embodiments, provided herein is polymorphic Form I of (R)—N-(5-(5-isopropyl-1,2,4-oxadiazol-3-yl)-2,3-dihydro-1H-inden-1-yl)-2-methyl-2H-tetrazole-5-carboxamide.

In some embodiments, Form I has an XRPD pattern substantially as shown in FIG. 1A. Angles 2-theta and relative peak intensities that may be observed for Form I using XRPD are shown in Table 1.

TABLE 1

| Angle/2θ | Intensity/% |
|---|---|
| 7.1 | 50.7 |
| 8.8 | 8.5 |
| 9.9 | 29 |
| 12.2 | 12.2 |
| 13.3 | 14.3 |
| 14.2 | 83.5 |
| 14.9 | 100 |
| 16.2 | 65.9 |
| 17.6 | 35.3 |
| 18.3 | 42.3 |
| 18.7 | 5.2 |
| 19.4 | 4.2 |
| 19.7 | 7.1 |
| 20.2 | 5.4 |
| 20.5 | 7.6 |
| 21.0 | 33.6 |
| 21.4 | 6.5 |
| 21.8 | 8.4 |
| 23.0 | 20.6 |
| 23.3 | 23.4 |
| 23.6 | 17.6 |
| 24.1 | 40 |
| 24.5 | 39.5 |
| 25.3 | 14.1 |
| 25.5 | 11.9 |
| 26.7 | 25.4 |
| 28.1 | 16.1 |
| 28.7 | 9.3 |
| 29.8 | 6.9 |
| 30.4 | 5.2 |

In some embodiments, polymorphic Form I has an XRPD pattern displaying at least two, at least three, at least four, at least five, at least six, at least seven, at least eight, at least nine, or at least ten of the peaks at angles 2-theta with the greatest intensity in the XRPD pattern substantially as shown in FIG. 1A or as provided in Table 1. It should be understood that relative intensities can vary depending on a number of factors, including sample preparation, mounting, and the instrument and analytical procedure and settings used to obtain the spectrum. Relative peak intensities and peak assignments can vary within experimental error. In some embodiments, peak assignments listed herein, including for polymorphic Form I, can vary by about ±0.6 degrees, ±0.4 degrees, ±0.2 degrees, or ±0.1 degrees 2-theta.

In some embodiments, polymorphic Form I has an XRPD pattern comprising peaks at angles 2-theta of 7.1±0.2, 8.8±0.2, 9.9±0.2, 12.2±0.2, 13.3±0.2, 14.2±0.2, 14.9±0.2, 16.2±0.2, 17.6±0.2, 18.3±0.2, 18.7±0.2, 19.4±0.2, 19.7±0.2, 20.2±0.2, 20.5±0.2, 21.0±0.2, 21.4±0.2, 21.8±0.2, 23.0±0.2, 23.3±0.2, 23.6±0.2, 24.1±0.2, 24.5±0.2, 25.3±0.2, 25.5±0.2, 26.7±0.2, 28.1±0.2, 28.7±0.2, 29.8±0.2, and 30.4±0.2 degrees. In some embodiments, polymorphic Form I has an XRPD pattern comprising peaks at angles 2-theta of 7.1±0.2, 9.9±0.2, 14.2±0.2, 14.9±0.2, 16.2±0.2, 17.6±0.2, 18.3±0.2, 21.0±0.2, 24.1±0.2, and 24.5±0.2 degrees. In some embodiments, polymorphic Form I has an XRPD pattern comprising peaks at angles 2-theta of 7.1±0.2, 14.2±0.2, 14.9±0.2, 16.2±0.2, and 18.3±0.2 degrees. It is to be understood that additional peaks in the XRPD pattern other than those shown in FIG. 1A or as provided in Table 1 may be observed, for instance, due to the presence of impurities, solvent, or other polymorphs or amorphic forms present in the test sample.

Figure 1B:
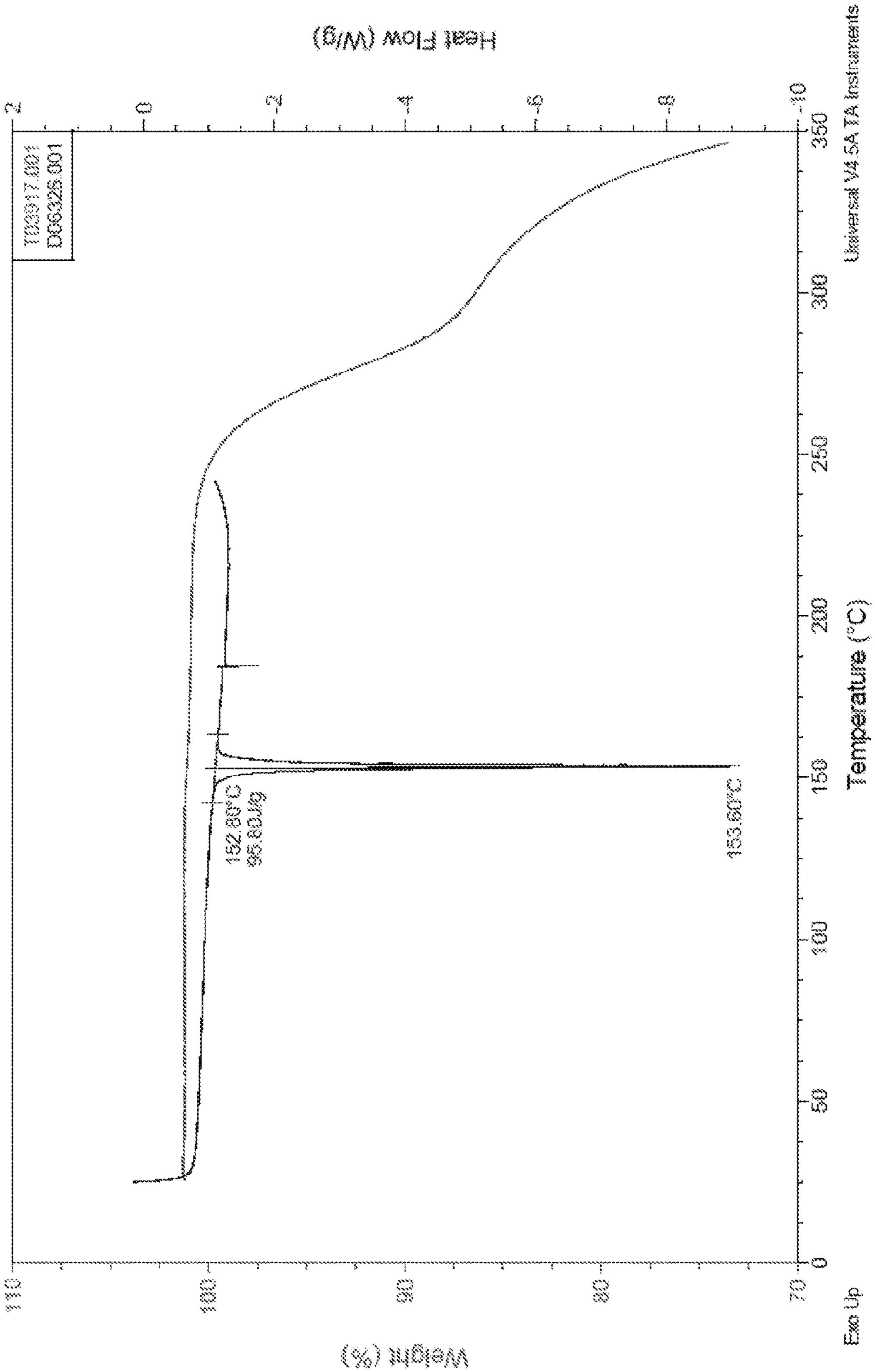
FIG. 1B shows differential scanning calorimetry (DSC) and thermal gravimetric analysis (TGA) graphs of polymorphic Form I of (R)—N-(5-(5-isopropyl-1,2,4-oxadiazol-3-yl)-2,3-dihydro-1H-inden-1-yl)-2-methyl-2H-tetrazole-5-carboxamide.

In some embodiments, Form I has a DSC graph substantially as shown in FIG. 1B. In some embodiments, Form I is characterized as having an endotherm onset at about 153° C. as determined by DSC. In some embodiments, Form I is characterized as having an endotherm onset at 153±2° C. (e.g., 153±1.9° C., 153±1.8° C., 153±1.7° C., 153±1.6° C., 153±1.5° C., 153±1.4° C., 153±1.3° C., 192±1.2° C., 153±1, 153±0.9° C., 153±0.8° C., 153±0.7° C., 153±0.6° C., 153±0.5° C., 153±0.4° C., 153±0.3° C., 153±0.2° C., or 153±0.1° C.) as determined by DSC.

In some embodiments, Form I has a TGA graph substantially as shown in FIG. 1B. In some embodiments, Form I is characterized as showing no weight loss prior to degradation, which starts at about 230° C., as determined by TGA.

Figure 1C:
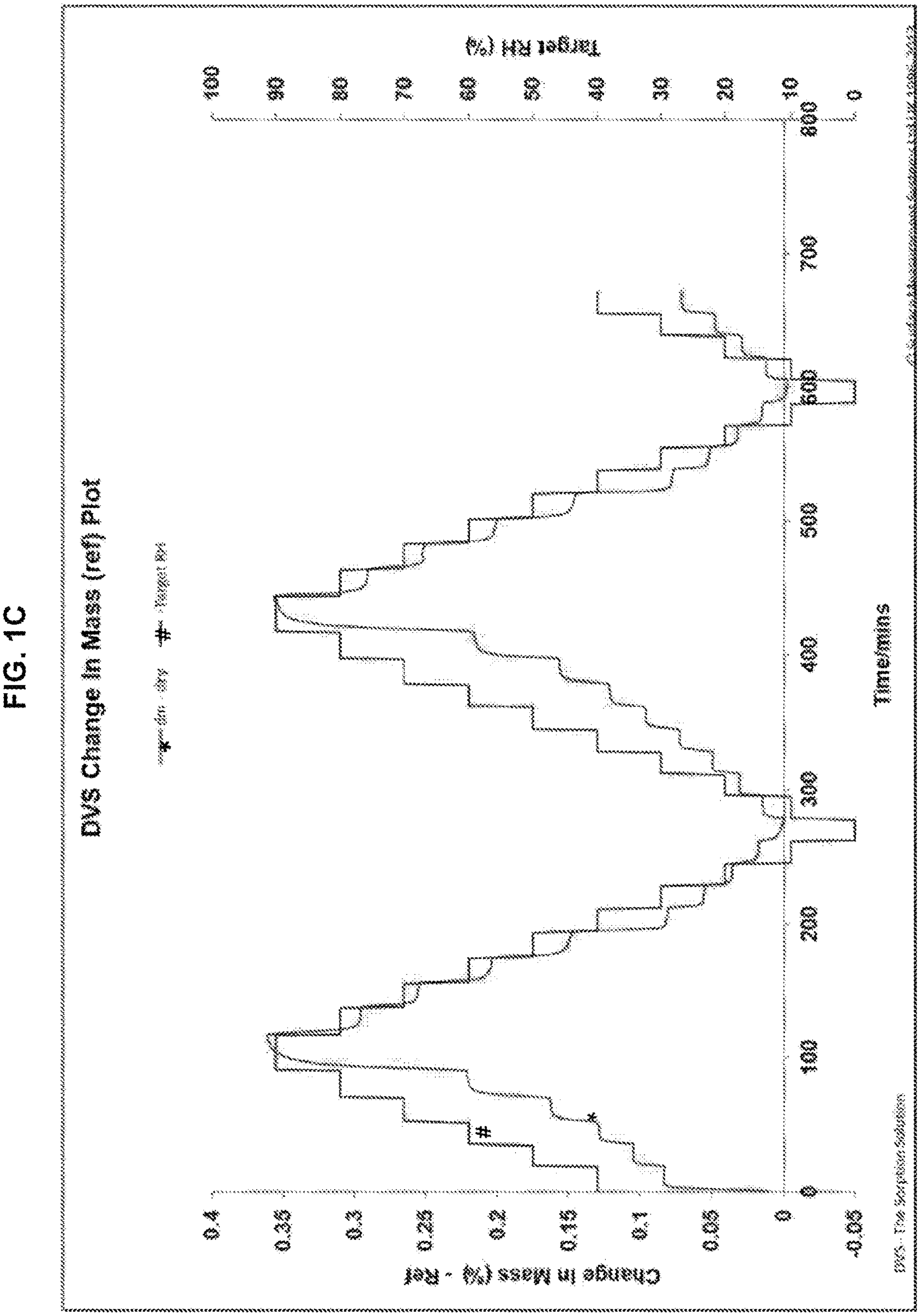
FIG. 1C shows a kinetic plot of Dynamic Vapor Sorption (DVS) graph of polymorphic Form I of (R)—N-(5-(5-isopropyl-1,2,4-oxadiazol-3-yl)-2,3-dihydro-1H-inden-1-yl)-2-methyl-2H-tetrazole-5-carboxamide.
Figure 1D:
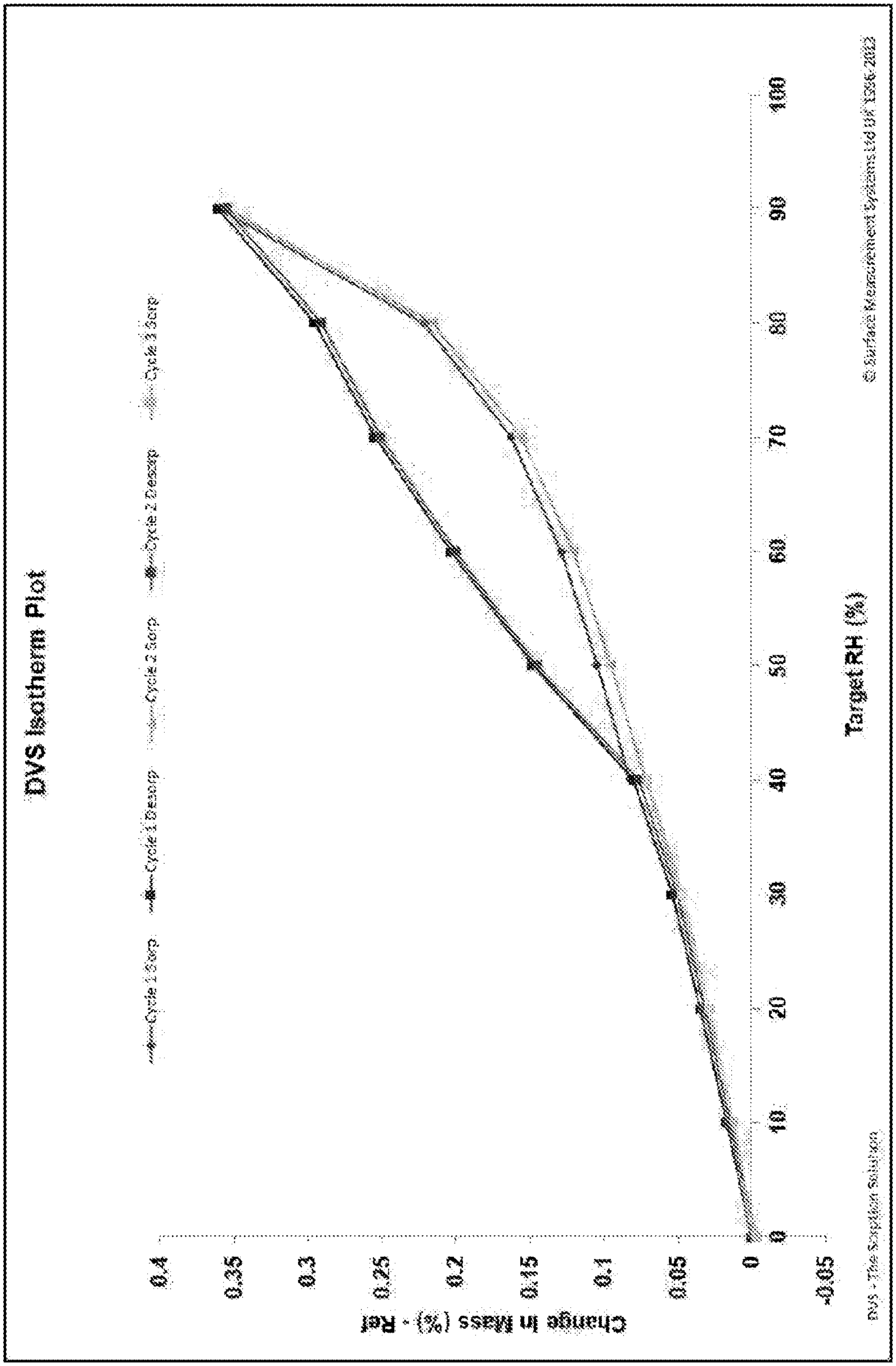
FIG. 1D shows an isotherm plot of DVS graph of polymorphic Form I of (R)—N-(5-(5-isopropyl-1,2,4-oxadiazol-3-yl)-2,3-dihydro-1H-inden-1-yl)-2-methyl-2H-tetrazole-5-carboxamide.

In some embodiments, Form I has a DVS graph substantially as shown in FIG. 1C or FIG. 1D. In some embodiments, Form I has a DVS graph substantially as shown in FIG. 1C. In some embodiments, Form I has a DVS graph substantially as shown in FIG. 1D.

In some embodiments of Form I, at least one, at least two, at least three, at least four, at least five, or all of the following (a)-(f) apply:

(a) Form I has an XRPD pattern comprising peaks at angles 2-theta of 7.1±0.2, 14.2±0.2, 14.9±0.2, 16.2±0.2, and 18.3±0.2 degrees; an XRPD pattern comprising peaks at angles 2-theta of 7.1±0.2, 9.9±0.2, 14.2±0.2, 14.9±0.2, 16.2±0.2, 17.6±0.2, 18.3±0.2, 21.0±0.2, 24.1±0.2, and 24.5±0.2 degrees; or an XRPD pattern comprising peaks at angles 2-theta of 7.1±0.2, 8.8±0.2, 9.9±0.2, 12.2±0.2, 13.3±0.2, 14.2±0.2, 14.9±0.2, 16.2±0.2, 17.6±0.2, 18.3±0.2, 18.7±0.2, 19.4±0.2, 19.7±0.2, 20.2±0.2, 20.5±0.2, 21.0±0.2, 21.4±0.2, 21.8±0.2, 23.0±0.2, 23.3±0.2, 23.6±0.2, 24.1±0.2, 24.5±0.2, 25.3±0.2, 25.5±0.2, 26.7±0.2, 28.1±0.2, 28.7±0.2, 29.8±0.2, and 30.4±0.2 degrees;

(b) Form I has an XRPD pattern substantially as shown in FIG. 1A;

(c) Form I has a DSC graph substantially as shown in FIG. 1B;

(d) Form I is characterized as having an endotherm onset at about 153° C. as determined by DSC;

(e) Form I has a TGA graph substantially as shown in FIG. 1B; and (f) Form I has a DVS graph substantially as shown in FIG. 1C or FIG. 1D.

Form II

In some embodiments, provided herein is polymorphic Form II of (R)—N-(5-(5-isopropyl-1,2,4-oxadiazol-3-yl)-2,3-dihydro-1H-inden-1-yl)-2-methyl-2H-tetrazole-5-carboxamide.

Figure 2A:
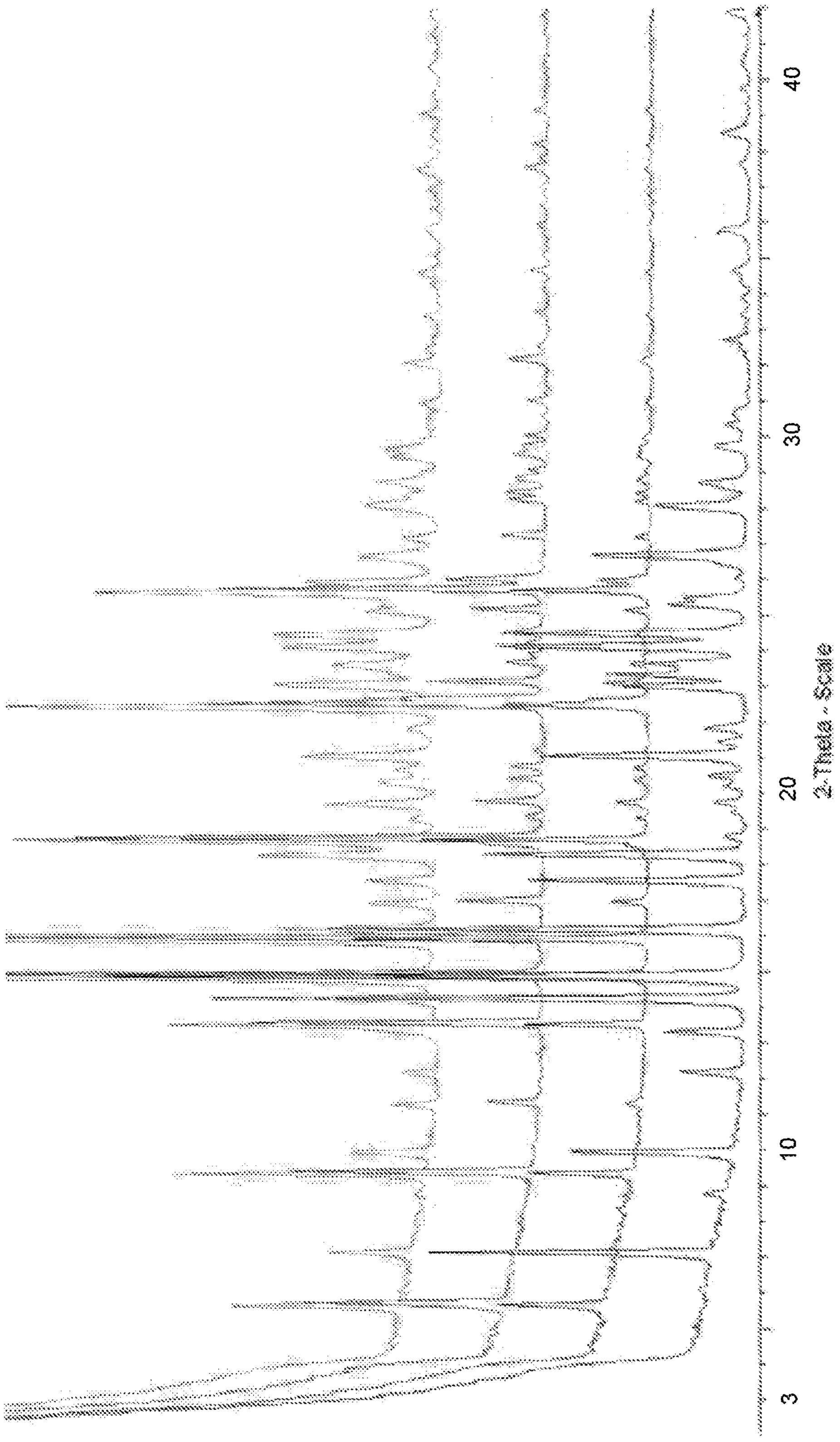
FIG. 2A shows XRPD patterns of polymorphic Form I and Form II of (R)—N-(5-(5-isopropyl-1,2,4-oxadiazol-3-yl)-2,3-dihydro-1H-inden-1-yl)-2-methyl-2H-tetrazole-5-carboxamide and their mixture (from top to bottom: mixture of Form I and Form II, Form II, Form II, Form I).

In some embodiments, Form II has an XRPD pattern substantially as shown in FIG. 2A. Angles 2-theta and relative peak intensities that may be observed for Form II using XRPD are shown in Table 2.

TABLE 2

| Angle/2θ | Intensity/% |
|---|---|
| 5.7 | 31.4 |
| 9.4 | 33.2 |
| 11.3 | 8.6 |
| 13.6 | 38.2 |
| 14.9 | 87.3 |
| 16.0 | 100 |
| 17.0 | 12.4 |
| 18.8 | 59.9 |
| 19.4 | 3.7 |
| 19.8 | 10.1 |
| 20.4 | 5.7 |
| 20.8 | 5.5 |
| 22.5 | 43.2 |
| 22.7 | 20.2 |
| 23.1 | 16 |
| 23.6 | 6.1 |
| 23.9 | 3.3 |

TABLE 2-continued

| Angle/2θ | Intensity/% |
|---|---|
| 24.2 | 3.9 |
| 24.5 | 5.7 |
| 25.1 | 10.5 |
| 25.8 | 42.1 |
| 26.0 | 13.6 |
| 27.3 | 6.7 |
| 28.3 | 5.6 |
| 28.5 | 6 |
| 28.8 | 4.9 |
| 29.5 | 5.3 |
| 29.8 | 4.2 |
| 30.1 | 3.8 |

In some embodiments, polymorphic Form II has an XRPD pattern displaying at least two, at least three, at least four, at least five, at least six, at least seven, at least eight, at least nine, or at least ten of the peaks at angles 2-theta with the greatest intensity in the XRPD pattern substantially as shown in FIG. 2A or as provided in Table 2. It should be understood that relative intensities can vary depending on a number of factors, including sample preparation, mounting, and the instrument and analytical procedure and settings used to obtain the spectrum. Relative peak intensities and peak assignments can vary within experimental error. In some embodiments, peak assignments listed herein, including for polymorphic Form II, can vary by about ±0.6 degrees, ±0.4 degrees, ±0.2 degrees, or ±0.1 degrees 2-theta.

In some embodiments, polymorphic Form II has an XRPD pattern comprising peaks at angles 2-theta of 5.7±0.2, 9.4±0.2, 11.3±0.2, 13.6±0.2, 14.9±0.2, 16.0±0.2, 17.0±0.2, 18.8±0.2, 19.4±0.2, 19.8±0.2, 20.4±0.2, 20.8±0.2, 22.5±0.2, 22.7±0.2, 23.1±0.2, 23.6±0.2, 23.9±0.2, 24.2±0.2, 24.5±0.2, 25.1±0.2, 25.8±0.2, 26.0±0.2, 27.3±0.2, 28.3±0.2, 28.5±0.2, 28.8±0.2, 29.5±0.2, 29.8±0.2, and 30.1±0.2 degrees. In some embodiments, polymorphic Form II has an XRPD pattern comprising peaks at angles 2-theta of 5.7±0.2, 9.4±0.2, 13.6±0.2, 14.9±0.2, 16.0±0.2, 18.8±0.2, 22.5±0.2, 22.7±0.2, 23.1±0.2, and 25.8±0.2 degrees. In some embodiments, polymorphic Form II has an XRPD pattern comprising peaks at angles 2-theta of 14.9±0.2, 16.0±0.2, 18.8±0.2, 22.5±0.2, and 25.8±0.2 degrees. It is to be understood that additional peaks in the XRPD pattern other than those shown in FIG. 2A or as provided in Table 2 may be observed, for instance, due to the presence of impurities, solvent, or other polymorphs or amorphic forms present in the test sample.

Figure 2B:
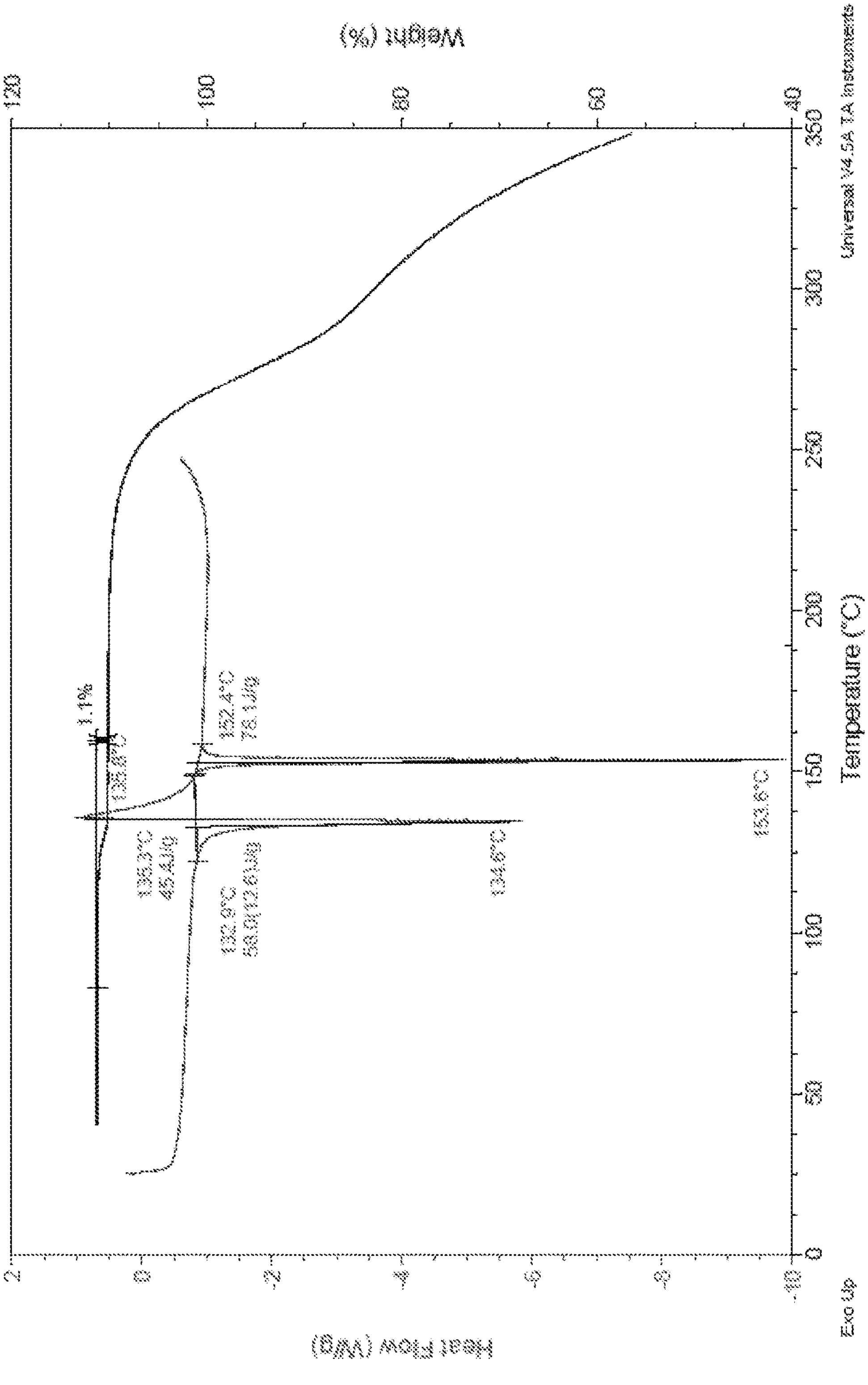
FIG. 2B shows DSC and TGA graphs of polymorphic Form II of (R)—N-(5-(5-isopropyl-1,2,4-oxadiazol-3-yl)-2,3-dihydro-1H-inden-1-yl)-2-methyl-2H-tetrazole-5-carboxamide. The sample was heated at 10° C./min when the DSC graph was measured.

In some embodiments, Form II has a DSC graph substantially as shown in FIG. 2B. In some embodiments, Form II is characterized as having an endotherm onset at about 133° C. as determined by DSC, and/or an exotherm onset at about 135° C. as determined by DSC, and/or an endotherm onset at about 152° C. as determined by DSC. In some embodiments, Form II is characterized as having an endotherm onset at 133±2° C. (e.g., 133±1.9° C., 133±1.8° C., 133±1.7° C., 133±1.6° C., 133±1.5° C., 133±1.4° C., 133±1.3° C., 192±1.2° C., 133±1, 133±0.9° C., 133±0.8° C., 133±0.7° C., 133±0.6° C., 133±0.5° C., 133±0.4° C., 133±0.3° C., 133±0.2° C., or 133±0.1° C.) as determined by DSC, and/or an exotherm onset at 135±2° C. (e.g., 135±1.9° C., 135±1.8° C., 135±1.7° C., 135±1.6° C., 135±1.5° C., 135±1.4° C., 135±1.3° C., 192±1.2° C., 135±1, 135±0.9° C., 135±0.8° C., 135±0.7° C., 135±0.6° C., 135±0.5° C., 135±0.4° C., 135±0.3° C., 135±0.2° C., or 135±0.1° C.) as determined by DSC, and/or an endotherm onset at 152±2° C. (e.g., 152±1.9° C., 152±1.8° C., 152±1.7° C., 152±1.6° C., 152±1.5° C., 152±1.4° C., 152±1.3° C., 192±1.2° C., 152±1, 152±0.9° C., 152±0.8° C., 152±0.7° C., 152±0.6° C., 152±0.5° C., 152±0.4° C., 152±0.3° C., 152±0.2° C., or 152±0.1° C.) as determined by DSC.

In some embodiments, Form II has a TGA graph substantially as shown in FIG. 2B. In some embodiments, Form II is characterized as showing a weight loss of about 1.1% between about 83° C. and about 160° C. prior to degradation, as determined by TGA.

Figure 2C:
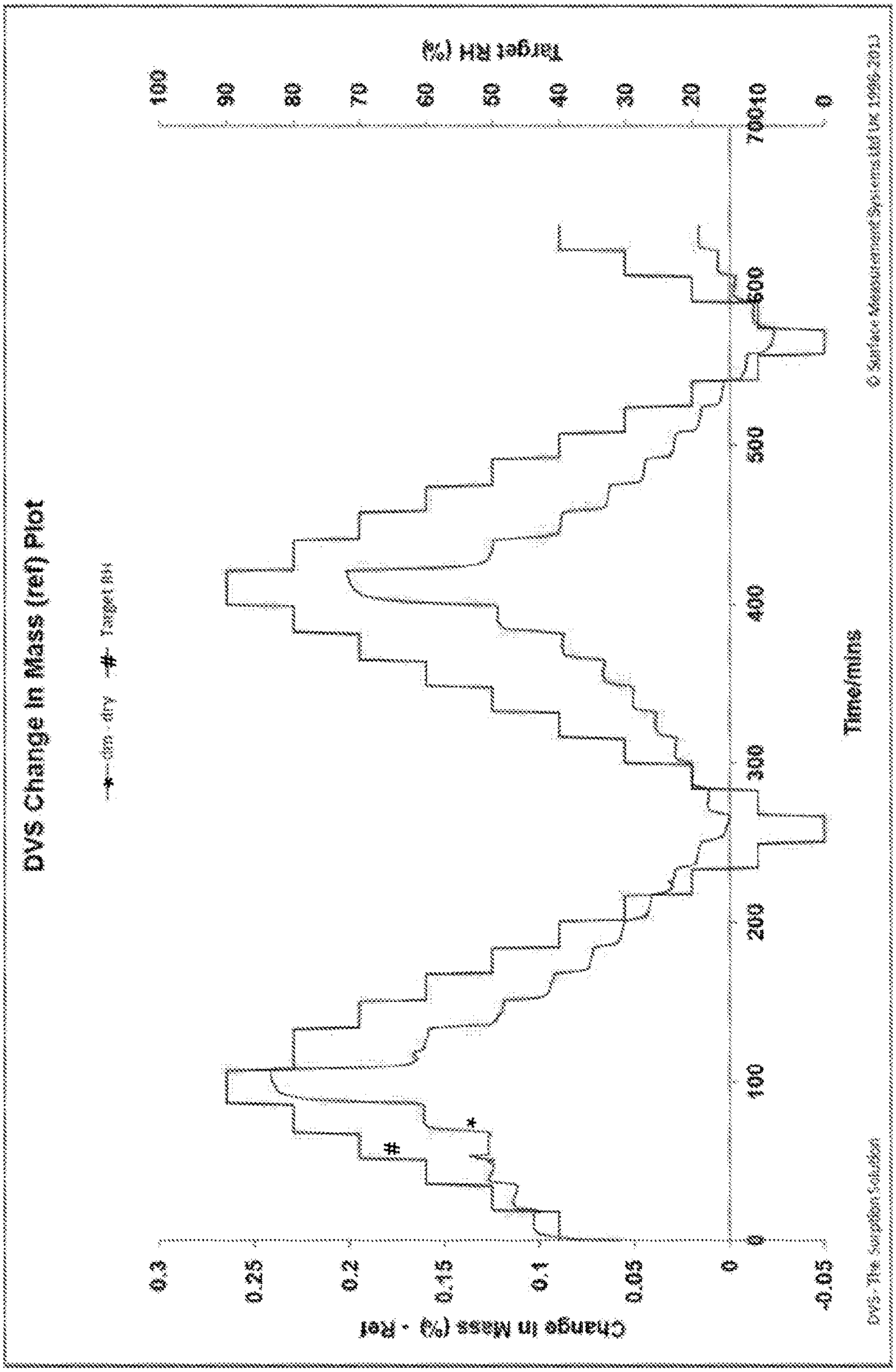
FIG. 2C shows a kinetic plot of DVS graph of polymorphic Form II of (R)—N-(5-(5-isopropyl-1,2,4-oxadiazol-3-yl)-2,3-dihydro-1H-inden-1-yl)-2-methyl-2H-tetrazole-5-carboxamide.
Figure 2D:
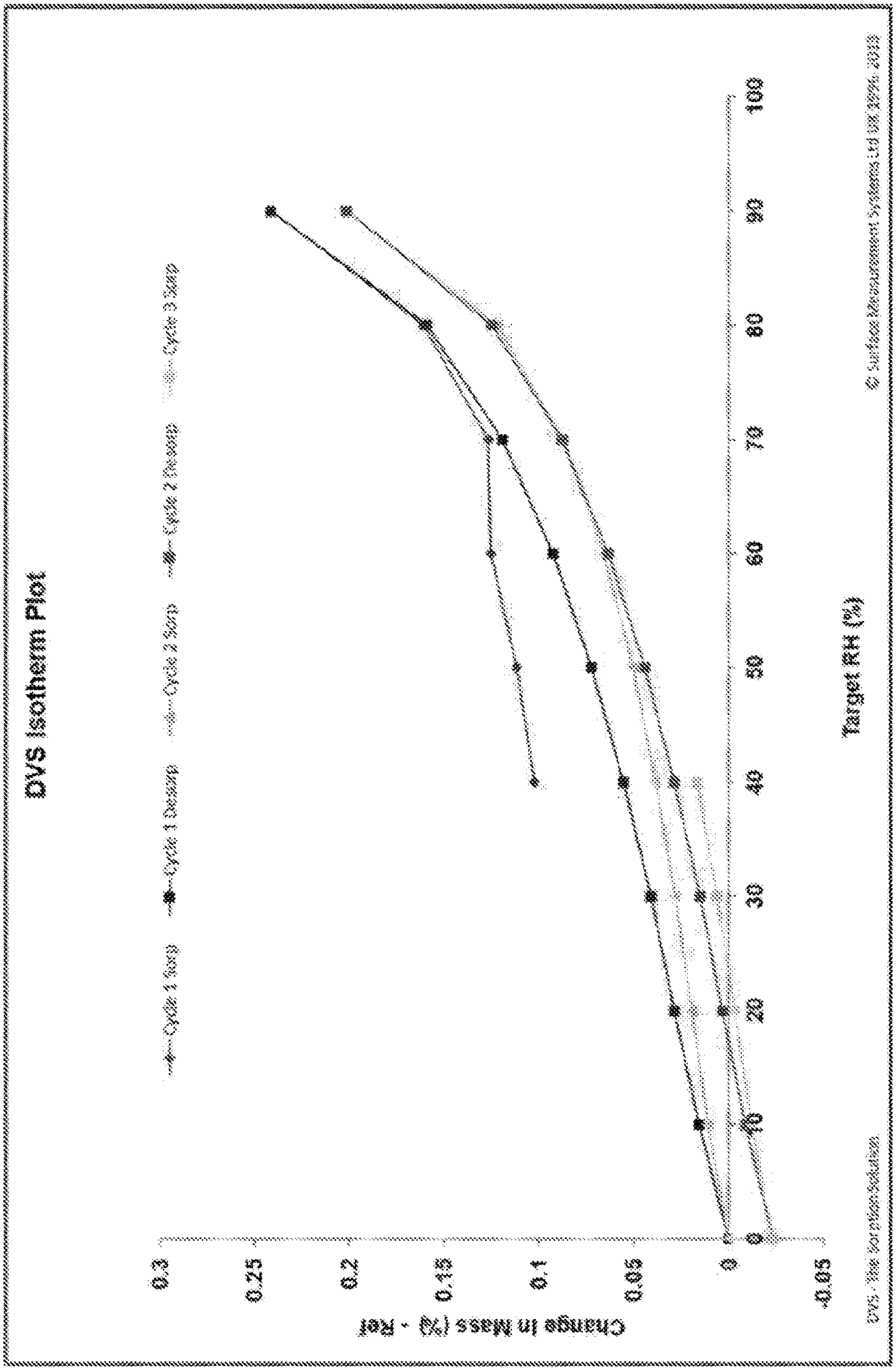
FIG. 2D shows an isotherm plot of DVS graph of polymorphic Form II of (R)—N-(5-(5-isopropyl-1,2,4-oxadiazol-3-yl)-2,3-dihydro-1H-inden-1-yl)-2-methyl-2H-tetrazole-5-carboxamide.

In some embodiments, Form II has a DVS graph substantially as shown in FIG. 2C or FIG. 2D. In some embodiments, Form II has a DVS graph substantially as shown in FIG. 2C. In some embodiments, Form II has a DVS graph substantially as shown in FIG. 2D.

In some embodiments of Form II, at least one, at least two, at least three, at least four, at least five, or all of the following (a)-(e) apply:

(a) Form II has an XRPD pattern comprising peaks at angles 2-theta of 14.9±0.2, 16.0±0.2, 18.8±0.2, 22.5±0.2, and 25.8±0.2 degrees; an XRPD pattern comprising peaks at angles 2-theta of 5.7±0.2, 9.4±0.2, 13.6±0.2, 14.9±0.2, 16.0±0.2, 18.8±0.2, 22.5±0.2, 22.7±0.2, 23.1±0.2, and 25.8±0.2 degrees; or an XRPD pattern comprising peaks at angles 2-theta of 5.7±0.2, 9.4±0.2, 11.3±0.2, 13.6±0.2, 14.9±0.2, 16.0±0.2, 17.0±0.2, 18.8±0.2, 19.4±0.2, 19.8±0.2, 20.4±0.2, 20.8±0.2, 22.5±0.2, 22.7±0.2, 23.1±0.2, 23.6±0.2, 23.9±0.2, 24.2±0.2, 24.5±0.2, 25.1±0.2, 25.8±0.2, 26.0±0.2, 27.3±0.2, 28.3±0.2, 28.5±0.2, 28.8±0.2, 29.5±0.2, 29.8±0.2, and 30.1±0.2 degrees;

(b) Form II has an XRPD pattern substantially as shown in FIG. 2A;

(c) Form II has a DSC graph substantially as shown in FIG. 2B;

(d) Form II has an endotherm onset at about 133° C. as determined by DSC, and/or an exotherm onset at about 135° C. as determined by DSC, and/or an endotherm onset at about 152° C. as determined by DSC;

(e) Form II has a TGA graph substantially as shown in FIG. 2B; and (f) Form II has a DVS graph substantially as shown in FIG. 2C or FIG. 2D.

Compositions

Also provided herein are compositions containing polymorphs described herein, such as Form I, Form II, or a mixture thereof. In some embodiments, the composition contains Form I. In some embodiments, the composition contains Form II. In some embodiment, the composition further comprises a pharmaceutically acceptable carrier.

In some embodiments, provided is a composition containing Form I of (R)—N-(5-(5-isopropyl-1,2,4-oxadiazol-3-yl)-2,3-dihydro-1H-inden-1-yl)-2-methyl-2H-tetrazole-5-carboxamide. In some embodiments, the composition is substantially free of polymorphic Forms II of (R)—N-(5-(5-isopropyl-1,2,4-oxadiazol-3-yl)-2,3-dihydro-1H-inden-1-yl)-2-methyl-2H-tetrazole-5-carboxamide. In some embodiments, the composition is substantially free of amorphous or non-crystalline form of (R)—N-(5-(5-isopropyl-1,2,4-oxadiazol-3-yl)-2,3-dihydro-1H-inden-1-yl)-2-methyl-2H-tetrazole-5-carboxamide. In some embodiments, the composition is substantially free of salts of (R)—N-(5-(5-isopropyl-1,2,4-oxadiazol-3-yl)-2,3-dihydro-1H-inden-1-yl)-2-methyl-2H-tetrazole-5-carboxamide.

In some embodiments of the composition containing Form I of (R)—N-(5-(5-isopropyl-1,2,4-oxadiazol-3-yl)-2,3-dihydro-1H-inden-1-yl)-2-methyl-2H-tetrazole-5-carboxamide, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of the total composition is Form I. In some embodiments of the composition containing Form I of (R)—N-(5-(5-isopropyl-1,2,4-oxadiazol-3-yl)-2,3-dihydro-1H-inden-1-yl)-2-methyl-2H-tetrazole-5-carboxamide, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of (R)—N-(5-(5-isopropyl-1,2,4-oxadiazol-3-yl)-2,3-dihydro-1H-inden-1-yl)-2-methyl-2H-tetrazole-5-carboxamide exists in Form I.

In some embodiments, provided is a composition containing Form II of (R)—N-(5-(5-isopropyl-1,2,4-oxadiazol-3-yl)-2,3-dihydro-1H-inden-1-yl)-2-methyl-2H-tetrazole-5-carboxamide. In some embodiments, the composition is substantially free of polymorphic Forms I of (R)—N-(5-(5-isopropyl-1,2,4-oxadiazol-3-yl)-2,3-dihydro-1H-inden-1-yl)-2-methyl-2H-tetrazole-5-carboxamide. In some embodiments, the composition is substantially free of amorphous or non-crystalline form of (R)—N-(5-(5-isopropyl-1,2,4-oxadiazol-3-yl)-2,3-dihydro-1H-inden-1-yl)-2-methyl-2H-tetrazole-5-carboxamide. In some embodiments, the composition is substantially free of salts of (R)—N-(5-(5-isopropyl-1,2,4-oxadiazol-3-yl)-2,3-dihydro-1H-inden-1-yl)-2-methyl-2H-tetrazole-5-carboxamide.

In some embodiments of the composition containing Form II of (R)—N-(5-(5-isopropyl-1,2,4-oxadiazol-3-yl)-2,3-dihydro-1H-inden-1-yl)-2-methyl-2H-tetrazole-5-carboxamide, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of the total composition is Form II. In some embodiments of the composition containing Form II of (R)—N-(5-(5-isopropyl-1,2,4-oxadiazol-3-yl)-2,3-dihydro-1H-inden-1-yl)-2-methyl-2H-tetrazole-5-carboxamide, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of (R)—N-(5-(5-isopropyl-1,2,4-oxadiazol-3-yl)-2,3-dihydro-1H-inden-1-yl)-2-methyl-2H-tetrazole-5-carboxamide exists in Form II.

In some embodiments, provided is a composition containing Form I and Form II of (R)—N-(5-(5-isopropyl-1,2,4-oxadiazol-3-yl)-2,3-dihydro-1H-inden-1-yl)-2-methyl-2H-tetrazole-5-carboxamide. In some embodiments, Form I and Form II are present in a weight ratio of 99 to 1, 90 to 10, 80 to 20, 70 to 30, 60 to 40, 50 to 50, 40 to 60, 30 to 70, 20 to 80, 10 to 90, or 1 to 99. In some embodiments, the weight ratio of Form I to Form II is between 90 to 10 and 99 to 1. In some embodiments of a composition containing Form I and Form II, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of the total composition is Form I. In some embodiments of a composition containing Form I and Form II, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of (R)—N-(5-(5-isopropyl-1,2,4-oxadiazol-3-yl)-2,3-dihydro-1H-inden-1-yl)-2-methyl-2H-tetrazole-5-carboxamide exists in Form I. In some embodiments of a composition containing Form I and Form II, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of the total composition is Form II. In some embodiments of a composition containing Form I and Form II, at least about 0.1%, at least about 0.3%, at least about 0.5%, at least about 0.8%, at least about 1.0%, at least about 5.0%, at least about 10%, at least about 20%, at least about 30%, at least about 40%, at least about 50%, at least about 60%, at least about 70%, at least about 80%, at least about 85%, at least about 90%, at least about 95%, at least about 96%, at least about 97%, at least about 98%, at least about 99%, or at least about 99.9% by weight of (R)—N-(5-(5-isopropyl-1,2,4-oxadiazol-3-yl)-2,3-dihydro-1H-inden-1-yl)-2-methyl-2H-tetrazole-5-carboxamide exists in Form II.

In some embodiments, provided is a tablet or capsule containing one or more of the polymorphic forms described herein (e.g., Form I, II, or a mixture thereof), and one or more pharmaceutically acceptable carriers. In some embodiments, provided is a tablet or capsule containing substantially pure polymorphic Form I of (R)—N-(5-(5-isopropyl-1,2,4-oxadiazol-3-yl)-2,3-dihydro-1H-inden-1-yl)-2-methyl-2H-tetrazole-5-carboxamide, and one or more pharmaceutically acceptable carriers. In some embodiments, provided is a tablet or capsule containing substantially pure polymorphic Form II of (R)—N-(5-(5-isopropyl-1,2,4-oxadiazol-3-yl)-2,3-dihydro-1H-inden-1-yl)-2-methyl-2H-tetrazole-5-carboxamide, and one or more pharmaceutically acceptable carriers.

Methods of Preparation

Form I

In some embodiments, provided is a method of preparing polymorphic Form I of (R)—N-(5-(5-isopropyl-1,2,4-oxadiazol-3-yl)-2,3-dihydro-1H-inden-1-yl)-2-methyl-2H-tetrazole-5-carboxamide, comprising: (1) forming a mixture of (R)—N-(5-(5-isopropyl-1,2,4-oxadiazol-3-yl)-2,3-dihydro-1H-inden-1-yl)-2-methyl-2H-tetrazole-5-carboxamide and a solvent; and (2) cooling or evaporating the mixture of step (1). In some embodiments, the solvent comprises an alcohol (e.g., methanol, ethanol, or propanol), an acetate (e.g., isopropyl acetate or ethyl acetate), an ether (e.g., methyl t-butyl ether, diethyl ether, or 2-methyl tetrahydrofuran), a ketone (e.g., methyl ethyl ketone or methyl isobutyl ketone), a nitrile (e.g., acetonitrile), an amide (e.g., N,N-Dimethylformamide), a non-aromatic hydrocarbon (e.g., hexane), an aromatic hydrocarbon (e.g., toluene), or water, or a mixture thereof. In some embodiments, the solvent comprises n-heptane, diethyl ether, ethyl acetate, isopropyl acetate (iProAc), methyl isobutyl ketone (MIBK), 2-propanol (IPA), methyl ethyl ketone (MEK), 1-propanol, acetone, ethanol (EtOH), dimethyl sulfoxide (DMSO), water, methanol (MeOH), tert-butyl methyl ether (TBME), cyclohexane, 1,4-dioxane, toluene, chloroform, 1,2-dimethoxyethane, tetrahydrofuran (THF), dichloromethane (DCM), 2-methoxyethanol, 2-methyl-1-propanol, N,N-Dimethylformamide (DMF), acetonitrile (MeCN), ethyleneglycol, nitromethane, or N-methylpyrrolidone (NMP), or a mixture thereof. In some embodiments, the solvent comprises acetonitrile. In some embodiments, step (1) comprises heating the mixture to an elevated temperature such as about 80° C., about 75° C., about 70° C., about 65° C., about 60° C., about 55° C., about 50° C., about 45° C., about 40° C., or about 35° C. In some embodiments, step (1) comprises heating the mixture to about 70° C. In some embodiments, an anti-solvent is added before step (2) is performed. In some embodiments, the anti-solvent is water or IPA. In some embodiments, the anti-solvent is water. In some embodiments, step (2) comprises cooling the mixture of step (1). In some embodiments, step (2) comprises evaporating the mixture of step (1). In some embodiments, step (2) comprises cooling the mixture of step (1) to a temperature lower than the temperature at which step (1) is performed, such as cooling the mixture of step (1) to about 20° C., about 15° C., about 10° C., about 5° C., about 0° C., about −5° C., about −10° C., about −15° C., or about −20° C. In some embodiments, step (2) comprises cooling the mixture of step (1) to ambient temperature. In some embodiments, step (1) comprises heating the mixture to about 70° C. and step (2) comprises cooling the mixture of step (1) to ambient temperature. It is understood that Form I may also be prepared using a suitable method as described in Example 3 below.

In some embodiments, a method of preparing polymorphic Form I of (R)—N-(5-(5-isopropyl-1,2,4-oxadiazol-3-yl)-2,3-dihydro-1H-inden-1-yl)-2-methyl-2H-tetrazole-5-carboxamide further comprises a method of preparing (R)—N-(5-(5-isopropyl-1,2,4-oxadiazol-3-yl)-2,3-dihydro-1H-inden-1-yl)-2-methyl-2H-tetrazole-5-carboxamide, which comprises: (a) reacting 2-methyl-2H-tetrazole-5-carboxylic acid with (R)-1-amino-2,3-dihydro-1H-indene-5-carbonitrile hydrochloride, thereby generating (R)—N-(5-cyano-2,3-dihydro-1H-inden-1-yl)-2-methyl-2H-tetrazole-5-carboxamide; (b) reacting (R)—N-(5-cyano-2,3-dihydro-1H-inden-1-yl)-2-methyl-2H-tetrazole-5-carboxamide with hydroxylamine, thereby generating (R,Z)—N-(5-(N'-hydroxycarbamimidoyl)-2,3-dihydro-1H-inden-1-yl)-2-methyl-2H-tetrazole-5-carboxamide; and (c) reacting (R,Z)—N-(5-(N'-hydroxycarbamimidoyl)-2,3-dihydro-1H-inden-1-yl)-2-methyl-2H-tetrazole-5-carboxamide with isobutyric acid, thereby generating (R)—N-(5-(5-isopropyl-1,2,4-oxadiazol-3-yl)-2,3-dihydro-1H-inden-1-yl)-2-methyl-2H-tetrazole-5-carboxamide.

Form II

In some embodiments, provided is a method of preparing polymorphic Form II of (R)—N-(5-(5-isopropyl-1,2,4-oxadiazol-3-yl)-2,3-dihydro-1H-inden-1-yl)-2-methyl-2H-tetrazole-5-carboxamide, comprising: (1) forming a mixture of polymorphic Form I of (R)—N-(5-(5-isopropyl-1,2,4-oxadiazol-3-yl)-2,3-dihydro-1H-inden-1-yl)-2-methyl-2H-tetrazole-5-carboxamide and a solvent; and (2) removing the solvent. In some embodiments, the solvent comprises an acetate (e.g., isopropyl acetate or ethyl acetate) In some embodiments, the solvent comprises n-propyl acetate. In some embodiments, step (1) comprises heating the mixture to an elevated temperature such as about 80° C., about 75° C., about 70° C., about 65° C., about 60° C., about 55° C., about 50° C., about 45° C., about 40° C., or about 35° C. In some embodiments, step (1) comprises heating the mixture to about 50° C. In some embodiments, the mixture of step (1) is stirred before step (2) is performed. In some embodiments, the mixture of step (1) is stirred for about 10 minutes, about 20 minutes, about 30 minutes, about 40 minutes, about 50 minutes, about 1 hour, about 2 hours, about 3 hours, about 4 hours, about 5 hours, or about 6 hours. In some embodiments, the mixture of step (1) is stirred for about 10 minutes. It is understood that Form I may also be prepared using a suitable method as described in Example 3 below.

Methods of Use

The polymorphic forms and compositions provided herein may be used to treat or prevent a disease or condition in an individual or subject.

Without being bound by theory, the polymorphic forms and compositions provided are believed to act by inhibiting myosin. This inhibition potentially decreases the number of independent myosin heads interacting with actin filaments reducing the amount of contraction. Reducing contraction of cardiac muscle can be important for the treatment of heart diseases in which over-contraction is an issue. In some embodiments, provided are methods of treating or preventing heart disease in an individual or subject, comprising administering to the individual or subject in need thereof a polymorphic form or composition provided herein. In some embodiments, provided are methods of treating or preventing heart disease in a subject in need thereof comprising administering to the subject a therapeutically effective amount of a polymorphic form or composition provided herein. In some embodiments, provided are methods of treating heart disease in a subject in need thereof comprising administering to the subject a therapeutically effective amount of a polymorphic form or composition provided herein. In some embodiments, provided are methods of treating an established or diagnosed heart disease in a subject in need thereof comprising administering to the subject a therapeutically effective amount of a polymorphic form or composition provided herein. In some embodiments, provided are methods of preventing heart disease in a subject in need thereof comprising administering to the subject a therapeutically effective amount of a polymorphic form or composition provided herein.

Also provided herein is the use of a polymorphic form or composition provided herein in the manufacture of a medicament for treatment of a heart disease in a subject. In some aspects, provided is a polymorphic form or composition as described herein for use in a method of treatment of the human or animal body by therapy. In some embodiments, provided herein is a polymorphic form, such as Form I or Form II, or composition thereof, for use in a method of treatment of the human or animal body by therapy. In some embodiments, provided herein is a polymorphic form, such as Form I or Form II, or composition thereof, for use in treating or preventing heart disease. In some embodiments, provided herein is a polymorphic form, such as Form I or Form II, or composition thereof, for use in treating heart disease. In some embodiments, provided herein is a polymorphic form, such as Form I or Form II, or composition thereof, for use in treating an established or diagnosed heart disease. In other embodiments, provided herein is a polymorphic form, such as Form I or Form II, or composition thereof, for use in preventing heart disease. In some embodiments, provided herein is a polymorphic form, such as Form I or Form II, or composition thereof, for use in treating a disease or condition associated with HCM. In some embodiments, provided herein is a polymorphic form, such as Form I or Form II, or composition thereof, for use in treating a disease or condition associated with secondary left ventricular wall thickening. In some embodiments, provided herein is a polymorphic form, such as Form I or Form II, or composition thereof, for use in ameliorating a symptom associated with heart disease. In other embodiments, provided herein is a polymorphic form, such as Form I or Form II, or composition thereof, for use in reducing the risk of a symptom associated with heart disease. In other embodiments, provided herein is a polymorphic form, such as Form I or Form II, or composition thereof, for use in treating a disease or condition associated with small left ventricular cavity, cavity obliteration, hyperdynamic left ventricular contraction, obstruction of blood flow out of the left ventricle, cardiac hypertrophy, small cardiac stroke volume, impaired relaxation of the left ventricle, high left ventricle filling pressure, myocardial ischemia, or cardiac fibrosis. In certain embodiments, provided herein is a polymorphic form, such as Form I or Form II, or composition thereof, for use in treating a disease or condition associated with small left ventricular cavity and cavity obliteration, hyperdynamic left ventricular contraction, myocardial ischemia, or cardiac fibrosis. In some embodiments, provided herein is a polymorphic form, such as Form I or Form II, or composition thereof, for use in treating muscular dystrophies. In some embodiments, provided herein is a polymorphic form, such as Form I or Form II, or composition thereof, for use in treating a glycogen storage disease. In other embodiments, provided herein is a polymorphic form, such as Form I or Form II, or composition thereof, for use in modulating the cardiac sarcomere, such as inhibiting the cardiac sarcomere. In yet other embodiments, provided herein is a polymorphic form, such as Form I or Form II, or composition thereof, for use in potentiating cardiac myosin.

In some embodiments, the subject is a mammal. In some embodiments, the subject is a mouse, rat, dog, cat, pig, sheep, horse, cow, or human. In some embodiments, the subject is a human. In some embodiments, the subject has an established or diagnosed heart disease. In some embodiments, the subject has established or diagnosed hypertrophic cardiomyopathy (HCM). In some embodiments, the subject is at risk for developing heart disease. In some embodiments, the subject has a mutation that increases risk for heart disease. In some embodiments, the subject has a mutation that increases risk for hypertrophic cardiomyopathy (HCM). In some embodiments, the mutation is a sarcomeric mutation. In some embodiments, the mutation is a mutation in myosin heavy chain β (MHC-β), cardiac muscle troponin T (cTnT), tropomyosin alpha-1 chain (TPM1), myosin-binding protein C cardiac-type (MYBPC3), cardiac troponin I (cTnI), myosin essential light chain (ELC), titin (TTN), myosin regulatory light chain 2 ventricular/cardiac muscle isoform (MLC-2), cardiac muscle alpha actin, muscle LIM protein (MLP), or protein kinase AMP-activated non-catalytic subunit gamma 2 (PRKAG2). In some embodiments, the mutation is a mutation in MHC-β. In some embodiments, the subject has established or diagnosed hypertrophic cardiomyopathy without a confirmed genetic etiology.

In some embodiments, the subject has a high risk of progressive symptoms. In some embodiments, the subject has a high risk of atrial fibrillation, ventricular tachyarrhythmias, stroke, and/or sudden death. In some embodiments, the subject has a reduced exercise capacity. In some embodiments, the reduced exercise capacity is as compared to an age-matched control population. In some embodiments, the subject is eligible for surgical intervention or percutaneous ablation to treat the heart disease.

In some embodiments, the heart disease is hypertrophic cardiomyopathy (HCM). In some embodiments, the heart disease is obstructive HCM. In some embodiments, the heart disease is nonobstructive HCM. In some embodiments, the HCM is associated with a sarcomeric mutation. In some embodiments, the HCM is associated with a non-sarcomeric mutation. In some embodiments, the heart disease is obstructive or nonobstructive HCM caused by sarcomeric and/or non-sarcomeric mutations. In some embodiments, the sarcomeric mutation is a mutation in a myosin heavy chain β (MHC-β), cardiac muscle troponin T (cTnT), tropomyosin alpha-1 chain (TPM1), myosin-binding protein C cardiac-type (MYBPC3), cardiac troponin I (cTnI), myosin essential light chain (ELC), titin (TTN), myosin regulatory light chain 2 ventricular/cardiac muscle isoform (MLC-2), cardiac muscle alpha actin, or muscle LIM protein (MLP). In some embodiments, the sarcomeric mutation is a mutation in MHC-β. In some embodiments, the non-sarcomeric mutation is a mutation in protein kinase AMP-activated non-catalytic subunit gamma 2 (PRKAG2).

In some embodiments, provided herein are methods of treating a disease or condition associated with HCM, comprising administering to the individual or subject in need thereof a polymorphic form or composition provided herein. In some embodiments, the disease or condition is Fabry's Disease, Danon Disease, mitochondrial cardiomyopathies, or Noonan Syndrome.

Also provided herein is the use of a polymorphic form or composition provided herein in the manufacture of a medicament for treatment of a disease or condition associated with HCM.

In some embodiments, the heart disease is heart failure with preserved ejection fraction (HFpEF). In some embodiments, the heart disease is diastolic dysfunction. In some embodiments, the heart disease is cardiomyopathy. In some embodiments, the heart disease is primary or secondary restrictive cardiomyopathy. In some embodiments, the heart disease is condition or symptoms caused by coronary artery disease. In some embodiments, the heart disease is myocardial infarction or angina pectoris. In some embodiments, the heart disease is left ventricular outflow tract obstruction. In some embodiments, the heart disease is hypertensive heart disease. In some embodiments, the heart disease is congenital heart disease. In some embodiments, the heart disease is cardiac ischemia and/or coronary heart disease. In some embodiments, the heart disease is diabetic heart disease. In other embodiments, the heart disease is congestive heart failure. In some embodiments, the heart disease is right heart failure. In other embodiments, the heart disease is cardiorenal syndrome. In some embodiments, the heart disease is infiltrative cardiomyopathy. In some embodiments, the heart disease is a condition that is or is related to cardiac senescence or diastolic dysfunction due to aging. In some embodiments, the heart disease is a condition that is or is related to left ventricular hypertrophy and/or concentric left ventricular remodeling.

In some embodiments, the provided are methods of treating a disease or condition associated with secondary left ventricular wall thickening in an individual or subject, comprising administering to the individual or subject in need thereof a polymorphic form or composition provided herein. In some embodiments, the disease is hypertension, valvular heart diseases (aortic stenosis, Mitral valve regurgitation), metabolic syndromes (diabetes, obesity), end stage renal disease, scleroderma, sleep apnea, amyloidosis, Fabry's disease, Friedreich Ataxia, Danon disease, Noonan syndrome, or Pompe disease.

Also provided herein is the use of a polymorphic form or composition provided herein in the manufacture of a medicament for treatment of a disease or condition associated with secondary left ventricular wall thickening.

In some embodiments, provided are methods of ameliorating a symptom associated with heart disease in a subject, comprising administering to the individual or subject in need thereof a polymorphic form or composition provided herein, wherein the symptom is one or more selected from poor or reduced cardiac elasticity, poor or reduced diastolic left ventricular relaxation, abnormal left atrial pressure (e.g., abnormally high left atrial pressure), paroxysmal or permanent atrial fibrillation, increased left atrial and pulmonary capillary wedge pressures, increased left ventricular diastolic pressures, syncope, ventricular relaxation during diastole, ventricular fibrosis, left ventricular hypertrophy, left ventricular mass, increased left ventricular wall thickness, left ventricular mid-cavity obstruction, increased systolic anterior motion of mitral valve, left ventricular outflow tract obstruction, chest pain, exertional dyspnea, pre-syncope, abnormal exercise capacity, and fatigue.

In some embodiments, the provided are methods of treating a disease or condition associated with small left ventricular cavity, cavity obliteration, hyperdynamic left ventricular contraction, obstruction of blood flow out of the left ventricle, cardiac hypertrophy, small cardiac stroke volume, impaired relaxation of the left ventricle, high left ventricle filling pressure, myocardial ischemia, or cardiac fibrosis in an individual or subject, comprising administering to the individual or subject in need thereof a polymorphic form or composition provided herein.

In some embodiments, the provided are methods of treating a disease or condition associated with small left ventricular cavity and cavity obliteration, hyperdynamic left ventricular contraction, myocardial ischemia, or cardiac fibrosis in an individual or subject, comprising administering to the individual or subject in need thereof a polymorphic form or composition provided herein.

Also provided herein is the use of a polymorphic form or composition provided herein in the manufacture of a medicament for treatment of a disease or condition associated with small left ventricular cavity and cavity obliteration, hyperdynamic left ventricular contraction, myocardial ischemia, or cardiac fibrosis.

In some embodiments, the provided are methods of treating muscular dystrophies in an individual or subject (e.g., Duchenne muscular dystrophy), comprising administering to the individual or subject in need thereof a polymorphic form or composition provided herein. Also provided herein is the use of a polymorphic form or composition provided herein in the manufacture of a medicament for treatment of muscular dystrophies (e.g., Duchenne muscular dystrophy).

In some embodiments, the provided are methods of treating a glycogen storage disease in an individual or subject, comprising administering to the individual or subject in need thereof a polymorphic form or composition provided herein. Also provided herein is the use of a polymorphic form or composition provided herein in the manufacture of a medicament for treatment of a glycogen storage disease.

Also provided are methods for modulating the cardiac sarcomere in an individual or subject which method comprises administering to an individual or subject in need thereof a therapeutically effective amount of at least one chemical entity as described herein. In some embodiments, provided are methods of inhibiting the cardiac sarcomere, comprising contacting the cardiac sarcomere with at least one chemical entity as described herein, such as a polymorphic form or composition provided herein. Additionally provided herein is the use of at least one chemical entity as described herein, such as a polymorphic form or composition provided herein in the manufacture of a medicament for inhibiting the cardiac sarcomere of an individual or subject.

Also provided are methods for potentiating cardiac myosin in an individual or subject which method comprises administering to an individual or subject in need thereof a therapeutically effective amount of at least one chemical entity as described herein such as a polymorphic form or composition provided herein. Additionally provided herein is the use of at least one chemical entity as described herein, such as a polymorphic form or composition provided herein in the manufacture of a medicament for potentiating cardiac myosin in an individual or subject.

In some embodiments, the methods provided herein further comprise monitoring the effectiveness of the treatment. Examples of indicators include, but are not limited to improvement in one or more of the following: New York Heart Association (NYHA) Functional Classification, exercise capacity, cardiac elasticity, diastolic left ventricular relaxation, left atrial pressure, paroxysmal or permanent atrial fibrillation, left atrial and pulmonary capillary wedge pressures, left ventricular diastolic pressures, syncope, ventricular relaxation during diastole, ventricular fibrosis, left ventricular hypertrophy, left ventricular mass, left ventricular wall thickness, left ventricular mid-cavity obstruction systolic anterior motion of mitral valve, left ventricular outflow tract obstruction, chest pain, exertional dyspnea, pre-syncope, abnormal exercise capacity, and fatigue. These indicators can be monitored by techniques known in the art including self-reporting; ECG, including ambulatory ECG; echocardiography; cardiac MRI; CT; biopsy; cardiopulmonary exercise testing (CPET); and actigraphy.

In some embodiments, the polymorphic forms or compositions described therein reduces the contractility of a cardiomyocyte. In some embodiments, the polymorphic forms or compositions reduce the contractility of a cardiomyocyte by greater than 40%, such as greater than 45%, 50%, 60%, 70%, 80%, or 90%. In some embodiments, the polymorphic forms or compositions reduce the contractility of a cardiomyocyte 40%-90%, such as 40%-80%, 40-70%, 50%-90%, 50%-80% or 50%-70%. In some embodiments, the polymorphic forms or compositions do not significantly alter calcium transients in the cardiomyocyte. In some embodiments, the polymorphic forms or compositions decrease the ATPase activity in a cardiomyocyte. Methods of measuring contractility, ATPase activity, and calcium transients are known in the art, for example, by calcium labeling, electrophysiological recordings, and microscopic imaging. In some embodiments, the polymorphic forms or compositions do not significantly inhibit or induce a cytochrome P450 (CYP) protein.

In some embodiments, the subject has a left ventricular wall that is thicker than normal prior to treatment. In some embodiments, the subject has a left ventricular wall thickness that is greater than 15 mm, such as greater than 18 mm, 20 mm, 22 mm, 25 mm, or 30 mm prior to treatment. In some embodiments, the left ventricular wall thickness is reduced by greater than 5%, such as greater than 8%, 10%, 12%, 15%, 20%, or 30% following treatment. Left ventricular wall thickness can be measured by methods known in the art, such as by echocardiography, CT scan, or a cardiac MRI.

In some embodiments, the subject has abnormal cardiac fibrosis prior to treatment. In some embodiments, the abnormal cardiac fibrosis is reduced by greater than 5%, such as greater than 8%, 10%, 12%, 15%, 20%, or 30% following treatment. Cardiac fibrosis can be measured by methods known in the art, such as by biopsy or a cardiac MRI.

In some embodiments, the subject has reduced exercise capacity prior to treatment. In some embodiments, the exercise capacity of the subject is increased by greater than 5%, such as greater than 8%, 10%, 12%, 15%, 20% or 30% following treatment. In some embodiments, the exercise capacity is measured by cardiopulmonary exercise testing (CPET). CPET measures changes in oxygen consumption ($VO_2$ max). Methods of measuring CPET and $VO_2$ max are well known in the art (Malhotra et al., JACC: Heart Failure, 2016, 4(8): 607-616; Guazzi et al., J Amer College Cardiol, 2017, 70 (13): 1618-1636; Rowin et al., JACC: Cariovasc Imaging, 2017, 10(11):1374-1386). In some embodiments, $VO_2$ max is improved by more than 1 mL/kg/$m^2$, such as more than 1.2 mL/kg/$m^2$, 1.4 mL/kg/$m^2$, 1.5 mL/kg/$m^2$, 1.7 mL/kg/$m^2$, 2 mL/kg/$m^2$, 2.2 mL/kg/$m^2$, 2.5 mL/kg/$m^2$, 3 mL/kg/$m^2$, 3.2 mL/kg/$m^2$, or 3.5 mL/kg/$m^2$ following treatment.

In some embodiments, the subject has a New York Heart Association (NYHA) Functional Classification of II, III, or IV prior to treatment. In some embodiments, the subject has a New York Heart Association (NYHA) Functional Classification of III or IV prior to treatment. In some embodiments, the subject has a New York Heart Association (NYHA) Functional Classification of IV prior to treatment. In some embodiments, the subject remains in the same NYHA functional class or has a reduced NYHA functional class following treatment.

In some embodiments, $VO_2$ max is improved by more than 1 mL/kg/$m^2$, such as more than 1.2 mL/kg/$m^2$, 1.4 mL/kg/$m^2$, 1.5 mL/kg/$m^2$, 1.7 mL/kg/$m^2$, or 2 mL/kg/$m^2$ and the subject has a reduced NYHA functional class following treatment. In some embodiments, $VO_2$ max is improved by more than 2.5 mL/kg/$m^2$, 3 mL/kg/$m^2$, 3.2 mL/kg/$m^2$, or 3.5 mL/kg/$m^2$ and the subject remains in the same NYHA functional class or has a reduced NYHA functional class following treatment.

In some embodiments, daily function and/or activity level of the subject is improved following treatment. Improved daily function and/or activity level may be measured, for example, by journaling or actigraphy, such as a FitBit or FitBit-like monitors.

In some embodiments, the subject has one or more of decreased shortness of breath, decreased chest pain, decreased arrhythmia burden, such as atrial fibrillation and ventricular arrhythmias, decreased incidence of heart failure, and decreased ventricular outflow obstruction following treatment.

Dosages

The polymorphic forms and compositions disclosed and/or described herein are administered at a therapeutically effective dosage, e.g., a dosage sufficient to provide treatment for the disease state. While human dosage levels have yet to be optimized for the chemical entities described herein, generally, a daily dose ranges from about 0.01 to 100 mg/kg of body weight; in some embodiments, from about 0.05 to 10.0 mg/kg of body weight, and in some embodiments, from about 0.10 to 1.4 mg/kg of body weight. Thus, for administration to a 70 kg person, in some embodiments, the dosage range would be about from 0.7 to 7000 mg per day; in some embodiments, about from 3.5 to 700.0 mg per day, and in some embodiments, about from 7 to 100.0 mg per day. The amount of the chemical entity administered will be dependent, for example, on the subject and disease state being treated, the severity of the affliction, the manner and schedule of administration and the judgment of the prescribing physician. For example, an exemplary dosage range for oral administration is from about 5 mg to about 500 mg per day, and an exemplary intravenous administration dosage is from about 5 mg to about 500 mg per day, each depending upon the pharmacokinetics.

A daily dose is the total amount administered in a day. A daily dose may be, but is not limited to be, administered each day, every other day, each week, every 2 weeks, every month, or at a varied interval. In some embodiments, the daily dose is administered for a period ranging from a single day to the life of the subject. In some embodiments, the daily dose is administered once a day. In some embodiments, the daily dose is administered in multiple divided doses, such as in 2, 3, or 4 divided doses. In some embodiments, the daily dose is administered in 2 divided doses.

Administration of the polymorphic forms and compositions described herein can be via any accepted mode of administration for therapeutic agents including, but not limited to, oral, sublingual, subcutaneous, parenteral, intravenous, intranasal, topical, transdermal, intraperitoneal, intramuscular, intrapulmonary, vaginal, rectal, or intraocular administration. In some embodiments, the polymorphic form or composition is administered orally or intravenously. In some embodiments, the polymorphic form or composition disclosed and/or described herein is administered orally.

Pharmaceutically acceptable compositions include solid, semi-solid, liquid and aerosol dosage forms, such as tablet, capsule, powder, liquid, suspension, suppository, and aerosol forms. The polymorphic forms disclosed and/or described herein can also be administered in sustained or controlled release dosage forms (e.g., controlled/sustained release pill, depot injection, osmotic pump, or transdermal (including electrotransport) patch forms) for prolonged timed, and/or pulsed administration at a predetermined rate. In some embodiments, the compositions are provided in unit dosage forms suitable for single administration of a precise dose.

The polymorphic forms described herein can be administered either alone or in combination with one or more conventional pharmaceutical carriers or excipients (e.g., mannitol, lactose, starch, magnesium stearate, sodium saccharine, talcum, cellulose, sodium crosscarmellose, glucose, gelatin, sucrose, magnesium carbonate). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate). Generally, depending on the intended mode of administration, the pharmaceutical composition will contain about 0.005% to 95%, or about 0.5% to 50%, by weight of a polymorphic form disclosed and/or described herein. Actual methods of preparing such dosage forms are known, or will be apparent, to those skilled in this art; for example, see *Remington's Pharmaceutical Sciences*, Mack Publishing Company, Easton, Pennsylvania.

In some embodiments, the compositions will take the form of a pill or tablet and thus the composition may contain, along with a polymorphic form disclosed and/or described herein, one or more of a diluent (e.g., lactose, sucrose, dicalcium phosphate), a lubricant (e.g., magnesium stearate), and/or a binder (e.g., starch, gum acacia, polyvinylpyrrolidine, gelatin, cellulose, cellulose derivatives). Other solid dosage forms include a powder, marume, solution or suspension (e.g., in propylene carbonate, vegetable oils or triglycerides) encapsulated in a gelatin capsule.

Liquid pharmaceutically administrable compositions can, for example, be prepared by dissolving, dispersing or suspending etc. a polymorphic form disclosed and/or described herein and optional pharmaceutical additives in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of the polymorphic form contained in such parenteral compositions depends, for example, on the physical nature of the polymorphic form, the activity of the polymorphic form and the needs of the subject. However, percentages of active ingredient of 0.01% to 10% in solution are employable, and may be higher if the composition is a solid which will be subsequently diluted to another concentration. In some embodiments, the composition will comprise from about 0.2 to 2% of a polymorphic form disclosed and/or described herein in solution.

Pharmaceutical compositions of the polymorphic forms and compositions described herein may also be administered to the respiratory tract as an aerosol or solution for a nebulizer, or as a microfine powder for insufflation, alone or in combination with an inert carrier such as lactose. In such a case, the particles of the pharmaceutical composition may have diameters of less than 50 microns, or in some embodiments, less than 10 microns.

In addition, pharmaceutical compositions can include a polymorphic form disclosed and/or described herein and one or more additional medicinal agents, pharmaceutical agents, adjuvants, and the like. Suitable medicinal and pharmaceutical agents include those described herein.

Kits

Also provided are articles of manufacture and kits containing any of the polymorphic forms or compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a polymorphic form or composition described herein and instructions for use. The kits may contain instructions for use in the treatment of a heart disease in an individual or subject in need thereof. A kit may additionally contain any materials or equipment that may be used in the administration of the polymorphic forms or composition, such as vials, syringes, or IV bags. A kit may also contain sterile packaging.

Combinations

The polymorphic forms and compositions described herein may be administered alone or in combination with other therapies and/or therapeutic agents useful in the treatment of the aforementioned disorders, diseases, or conditions.

The polymorphic forms and compositions described herein may be combined with one or more other therapies to treat a heart disease, such as HCM or HFpEF. In some embodiments, the one or more therapies include therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors). In some embodiments, the one or more therapies include therapies that improve cardiac function by stimulating cardiac contractility (e.g., positive inotropic agents, such as the β-adrenergic agonist dobutamine or the phosphodiesterase inhibitor milrinone). In other embodiments, the one or more therapies include therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The polymorphic forms and compositions described herein may be combined with one or more other therapies to treat HCM or HFpEF. In some embodiments, the polymorphic forms and/compositions may be combined with a β-blocker, verapamil, and/or disopyramide.

Some exemplary embodiments are provided below:

1. A polymorph of (R)—N-(5-(5-isopropyl-1,2,4-oxadiazol-3-yl)-2,3-dihydro-1H-inden-1-yl)-2-methyl-2H-tetrazole-5-carboxamide.
2. The polymorph of embodiment 1, characterized by having an XRPD pattern comprising peaks at angles 2-theta of 7.1±0.2, 14.2±0.2, 14.9±0.2, 16.2±0.2, and 18.3±0.2 degrees.
3. The polymorph of embodiment 1 or 2, characterized by having an XRPD pattern comprising peaks at angles 2-theta of 7.1±0.2, 9.9±0.2, 14.2±0.2, 14.9±0.2, 16.2±0.2, 17.6±0.2, 18.3±0.2, 21.0±0.2, 24.1±0.2, and 24.5±0.2 degrees.
4. The polymorph of any one of embodiments 1-3, characterized by having an XRPD pattern substantially as shown in FIG. 1A.
5. The polymorph of any one of embodiments 1-4, characterized by having a DSC graph substantially a shown in FIG. 1B.
6. The polymorph of any one of embodiments 1-5, characterized by having an endotherm onset at about 153° C. as determined by DSC.
7. The polymorph of any one of embodiments 1-6, characterized by having a TGA graph substantially as shown in FIG. 1B.
8. The polymorph of any one of embodiments 1-7, characterized by having a DVS graph substantially as shown in FIG. 1C or FIG. 1D.
9. The polymorph of embodiment 1, characterized as having an XRPD pattern comprising peaks at angles 2-theta of 14.9±0.2, 16.0±0.2, 18.8±0.2, 22.5±0.2, and 25.8±0.2 degrees.
10. The polymorph of embodiment 1 or 9, characterized as having an XRPD pattern comprising peaks at angles 2-theta of 5.7±0.2, 9.4±0.2, 13.6±0.2, 14.9±0.2, 16.0±0.2, 18.8±0.2, 22.5±0.2, 22.7±0.2, 23.1±0.2, and 25.8±0.2 degrees.
11. The polymorph of any one of embodiments 1, 9 and 10, characterized as having an XRPD pattern substantially as shown in FIG. 2A.
12. The polymorph of any one of embodiments 1 and 9-11, characterized as having a DSC graph substantially as shown in FIG. 2B.
13. The polymorph of any one of embodiments 1 and 9-12, characterized as having an endotherm onset at about 133° C. as determined by DSC, and/or an exotherm onset at about 135° C. as determined by DSC, and/or an endotherm onset at about 152° C. as determined by DSC.
14. The polymorph of any one of embodiments 1 and 9-13, characterized as having a TGA graph substantially as shown in FIG. 2B.
15. The polymorph of any one of embodiments 1 and 9-14, characterized as having a DVS graph substantially as shown in FIG. 2C or FIG. 2D.
16. A method of preparing a polymorph of any one of embodiments 2-8, comprising:
   (1) forming a mixture of (R)—N-(5-(5-isopropyl-1,2,4-oxadiazol-3-yl)-2,3-dihydro-1H-inden-1-yl)-2-methyl-2H-tetrazole-5-carboxamide and a solvent; and
   (2) cooling or evaporating the mixture of step (1).
17. The method of embodiment 16, wherein the solvent comprises acetonitrile.
18. The method of embodiment 16 or 17, wherein step (1) comprises heating the mixture to about 70° C.
19. The method of any one of embodiments 16-18, wherein step (2) comprises cooling the mixture of step (1) to ambient temperature.
20. The method of any one of embodiments 16-19, wherein an anti-solvent is added before step (2) is performed, wherein the anti-solvent is water.
21. A method of preparing a polymorph of any one of embodiments 9-15, comprising:
   (1) forming a mixture of polymorphic Form I of (R)—N-(5-(5-isopropyl-1,2,4-oxadiazol-3-yl)-2,3-dihydro-1H-inden-1-yl)-2-methyl-2H-tetrazole-5-carboxamide and a solvent; and
   (2) removing the solvent.
22. The method of embodiment 21, wherein the solvent comprises n-propyl acetate.
23. The method of embodiment 21 or 22, wherein step (1) comprises heating the mixture to about 50° C.
24. A pharmaceutical composition comprising the polymorph of any one of embodiments 1-15, and a pharmaceutically acceptable excipient.
25. A method of treating heart disease in a subject in need thereof, comprising administering to the subject the polymorph of any one of embodiments 1-15, or the pharmaceutical composition of embodiment 24.
26. The method of embodiment 25, wherein the heart disease is hypertrophic cardiomyopathy (HCM).
27. The method of embodiment 26, wherein the HCM is obstructive or nonobstructive or is associated with a sarcomeric and/or non-sarcomeric mutation.
28. The method of embodiment 25, wherein the heart disease is heart failure with preserved ejection fraction (HFpEF).
29. The method of embodiment 25, wherein the heart disease is selected from the group consisting of diastolic dysfunction, primary or secondary restrictive cardiomyopathy, myocardial infarction and angina pectoris, left ventricular outflow tract obstruction, hypertensive heart disease, congenital heart disease, cardiac ischemia, coronary heart disease, diabetic heart disease, congestive heart failure, right heart failure, cardiorenal syndrome, and infiltrative cardiomyopathy.

30. The method of embodiment 25, wherein the heart disease is or is related to one or more conditions selected from the group consisting of cardiac senescence, diastolic dysfunction due to aging, left ventricular hypertrophy and concentric left ventricular remodeling.
31. A method of treating a disease or condition associated with HCM in a subject in need thereof, comprising administering to the subject the polymorph of any one of embodiments 1-15, or the pharmaceutical composition of embodiment 24.
32. The method of embodiment 31, wherein the disease or condition is selected from the group consisting of Fabry's Disease, Danon Disease, mitochondrial cardiomyopathies, and Noonan Syndrome.
33. A method of treating a disease or condition that is associated with secondary left ventricular wall thickening in a subject in need thereof, comprising administering to the subject the polymorph of any one of embodiments 1-15, or the pharmaceutical composition of embodiment 24.
34. The method of embodiment 33, wherein the disease or condition is selected from the group consisting of hypertension, valvular heart diseases, metabolic syndromes, end stage renal disease, scleroderma, sleep apnea, amyloidosis, Fabry's disease, Friedreich Ataxia, Danon disease, Noonan syndrome, and Pompe disease.
35. A method of treating a disease or condition that is associated with small left ventricular cavity and cavity obliteration, hyperdynamic left ventricular contraction, myocardial ischemia, or cardiac fibrosis in a subject in need thereof, comprising administering to the subject the polymorph of any one of embodiments 1-15, or the pharmaceutical composition of embodiment 24.
36. A method of treating a disease or condition selected from muscular dystrophies and glycogen storage diseases in a subject in need thereof, comprising administering to the subject the polymorph of any one of embodiments 1-15, or the pharmaceutical composition of embodiment 24.
37. A method of inhibiting the cardiac sarcomere, comprising contacting the cardiac sarcomere with the polymorph of any one of embodiments 1-15, or the pharmaceutical composition of embodiment 24.

EXAMPLES

The following examples are provided to further aid in understanding the embodiments disclosed in the application, and presuppose an understanding of conventional methods well known to those persons having ordinary skill in the art to which the examples pertain. The particular materials and conditions described hereunder are intended to exemplify particular aspects of embodiments disclosed herein and should not be construed to limit the reasonable scope thereof.

The following abbreviations may be used herein:

| | |
|---|---|
| XRPD | X-Ray Powder Diffraction |
| DSC | Differential Scanning Calorimetry |
| TGA | Thermal Gravimetric Analysis |
| DVS | Dynamic Vapor Sorption |
| 2-MeTHF | 2-Methyltetrahydrofuran |
| equiv. or eq. | Equivalents |

-continued

| | |
|---|---|
| vol | Volumes |
| RH | Relative humidity |
| ca. | Approximately |
| RT | Room Temperature |
| MEK | Methyl ethyl ketone |
| iProAc | Isopropyl acetate |
| MIBK | Methyl isobutyl ketone |
| EtOH | Ethanol |
| DMSO | Dimethyl sulfoxide |
| TBME | tert-Butyl methyl ether |
| THF | Tetrahydrofuran |
| DCM | dichloromethane |
| MeOH | Methanol |
| DMF | N,N-Dimethylformamide |
| MeCN | Acetonitrile |
| NMP | N-Methylpyrrolidone |
| IPA | 2-Propanol |

The polymorphic forms of (R)—N-(5-(5-isopropyl-1,2,4-oxadiazol-3-yl)-2,3-dihydro-1H-inden-1-yl)-2-methyl-2H-tetrazole-5-carboxamide were characterized by various analytical techniques, including XRPD, DSC, and TGA using the procedures described below.

XRPD

XRPD diffractograms were collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel$^{3D}$ detector, placed on the diffracted beam, was fitted with a receiving slit and 0.04 rad Soller slits. The software used for data collection was X'Pert Data Collector using X'Pert Operator Interface. The data were analysed and presented using Diffrac Plus EVA or HighScore Plus.

Samples were prepared and analyzed in either a metal or Millipore 96 well-plate in transmission mode. X-ray transparent film was used between the metal sheets on the metal well-plate and powders (approximately 1-2 mg) were used as received. The Millipore plate was used to isolate and analyze solids from suspensions by adding a small amount of suspension directly to the plate before filtration under a light vacuum.

The scan mode for the metal plate used the gonio scan axis, whereas a 2θ scan was utilized for the Millipore plate.

The details of the standard screening data collection method are:

Angular range: 2.5 to 32.0° 2θ;

Step size: 0.0130° 2θ;

Collection time: 12.75 s/step (total collection time of 2.07 min).

DSC

DSC data were collected on a TA Instruments Q2000 equipped with a 50 position auto-sampler or a TA Instruments Discovery DSC equipped with a 50 position auto-sampler. Typically, 0.5-3 mg of each sample, in a pin-holed aluminium pan, was heated at 10° C./min from 25° C. to 350° C. A purge of dry nitrogen at 50 ml/min was maintained over the sample. The instrument control software was TRIOS and the data were analyzed using TRIOS or Universal Analysis. For TA Instruments Q2000, the instrument control software was Advantage for Q Series and Thermal Advantage and the data were analyzed using Universal Analysis or TRIOS. For TA Instruments Discovery DSC, the instrument control software was TRIOS and the data were analyzed using TRIOS or Universal Analysis.

TGA

TGA data were collected on a TA Instruments Q500 TGA equipped with a 16 position auto-sampler or a TA Instruments Discovery TGA equipped with a 25 position auto-sampler. For TA Instruments Q500 TGA, typically 5-10 mg of each sample was loaded onto a pre-tared aluminium DSC pan and heated at 10° C./min from ambient temperature to 350° C. A nitrogen purge at 60 ml/min was maintained over the sample. The instrument control software was Advantage for Q Series and Thermal Advantage and the data were analyzed using Universal Analysis or TRIOS. For TA Instruments Discovery TGA, typically 5-10 mg of each sample was loaded onto a pre-tared aluminium DSC pan and heated at 10° C./min from ambient temperature to 350° C. A nitrogen purge at 25 ml/min was maintained over the sample. The instrument control software was TRIOS and the data were analyzed using TRIOS or Universal Analysis.

DVS

DVS data were obtained using a SMS DVS Intrinsic moisture sorption analyzer, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy ±0.005 mg).

Typically, 5-30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite.

Method Parameters for SMS DVS Intrinsic Experiments

| Parameters | Values |
|---|---|
| Adsorption-Scan 1 | 40-90 |
| Desorption, Adsorption-Scan 2 | 90-0, 0-40 |
| Intervals (% RH) | 10 |
| Number of Scans | 4 |
| Flow rate (ml/min) | 200 |
| Temperature (° C.) | 25 |
| Stability (° C./min) | 0.2 |
| Sorption Time (hours) | 6 hour time out |
| Number of cycles | 2 |

Example 1. Preparation of Form I

Polymorphic Form I of (R)—N-(5-(5-isopropyl-1,2,4-oxadiazol-3-yl)-2,3-dihydro-1H-inden-1-yl)-2-methyl-2H-tetrazole-5-carboxamide was prepared according to the scheme provided below.

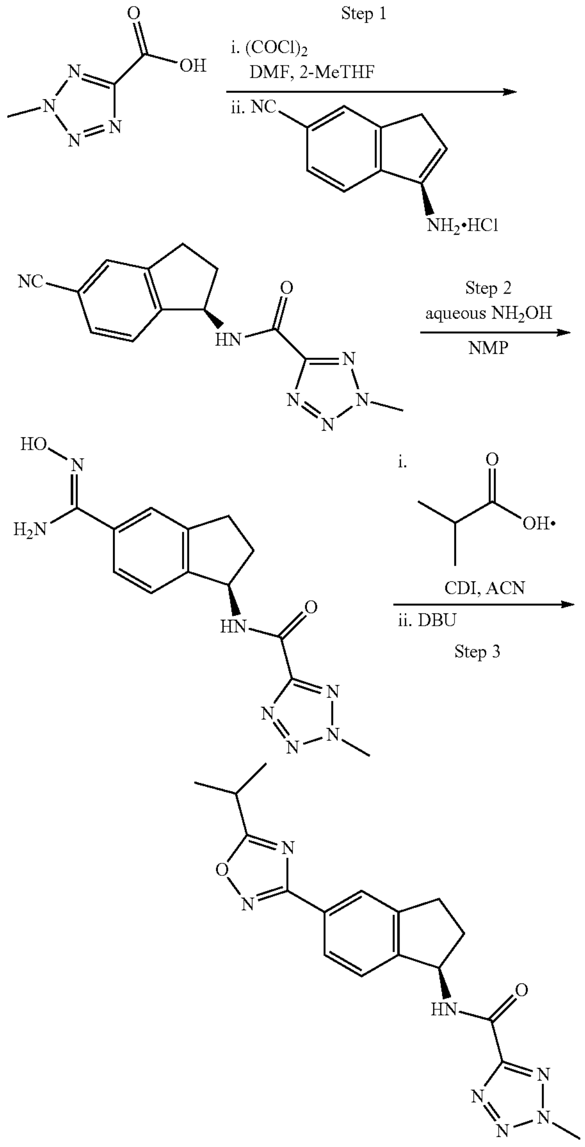

Step 1: preparation of (R)—N-(5-cyano-2,3-dihydro-1H-inden-1-yl)-2-methyl-2H-tetrazole-5-carboxamide. A mixture of 2-methyl-2H-tetrazole-5-carboxylic acid (78.7 g, 0.614 mol, 1.2 equiv.) and N,N-Dimethylforamide (0.4 mL, 0.005 mol, 0.01 equiv.) in 2-MeTHF (630 mL, 6.3 vol.) was stirred at ambient temperature. Oxalyl chloride (50.7 mL, 0.591 mol, 1.15 equiv.) was added slowly and the reaction mixture was stirred until ≤15% of the starting material 2-methyl-2H-tetrazole-5-carboxylic acid remained. A mixture of (R)-1-amino-2,3-dihydro-1H-indene-5-carbonitrile hydrochloride (100 g, 0.514 mol, 1.0 equiv.) in 2-MeTHF (630 mL. 6.3 vol.) was treated with a sodium hydroxide solution (72.2 g, 1805 mmol, 3.5 equiv.) in water (510 mL) at ambient temperature. The resultant mixture was stirred at ambient temperature for at least 30 minutes (Vessel 2). The freshly prepared 2-methyl-2H-tetrazole-5-carboxylic acid acid chloride solution was added to the reaction mixture while maintaining a temperature <30° C. The acid chloride solution was rinsed forward with 2-MeTHF (65 mL, 0.65 vol.). After complete addition, the mixture was allowed to react at ambient temperature until ≤5% of the intermediate (R)-1-amino-2,3-dihydro-1H-indene-5-carbonitrile hydrochloride remained. Upon confirming the reaction endpoint, n-heptane (950 mL, 9.5 vol.) is added over 1 hour. The mixture was then filtered. The resultant filter cake was washed with water (3×630 mL, 6.3 vol.). Then, the solid was dried and isolated. Obtained 126.5 g (91.8%) of (R)—N-(5-cyano-2,3-dihydro-1H-inden-1-yl)-2-methyl-2H-tetrazole-5-carboxamide.

Step 2: preparation of (R,Z)—N-(5-(N'-hydroxycarbamimidoyl)-2,3-dihydro-1H-inden-1-yl)-2-methyl-2H-tetrazole-5-carboxamide. Aqueous hydroxylamine (90.0 mL, 1.47 mol, 3.2 equiv.) was added slowly to a solution of (R)—N-(5-cyano-2,3-dihydro-1H-inden-1-yl)-2-methyl-2H-tetrazole-5-carboxamide (121.3 g, 0.452 mol, 1.0 equiv.) in N-methyl-2-pyrrolidinone (NMP, 600 mL, 5.0 vol.). The resulting mixture was agitated at ambient temperature until reaction completion (≤2% CK-3831269 remaining). The reaction mixture was quenched with water (1200 mL, 10 vol.) while maintaining the temperature below 40° C. and the resultant mixture is filtered. The filter cake is washed with water (3×600 mL, 5 vol.) and dried under vacuum at ambient temperature and isolated. Obtained 129.8 g (95.3%) of (R,Z)—N-(5-(N'-hydroxycarbamimidoyl)-2,3-dihydro-1H-inden-1-yl)-2-methyl-2H-tetrazole-5-carboxamide.

Step 3: preparation of polymorphic Form I of (R)—N-(5-(5-isopropyl-1,2,4-oxadiazol-3-yl)-2,3-dihydro-1H-inden-1-yl)-2-methyl-2H-tetrazole-5-carboxamide. A mixture of isobutyric acid (310.3 g, 3.52 mol, 1.10 equiv.) and 1,1'-carbonyldiimidazole (CDI, 549.5 g, 3.39 mol, 1.06 equiv.) in acetonitrile (7.65 kg) was stirred at ambient temperature until not more than 20% of the unreacted acid remained. (R,Z)—N-(5-(N'-hydroxycarbamimidoyl)-2,3-dihydro-1H-inden-1-yl)-2-methyl-2H-tetrazole-5-carboxamide (964 g, 3.20 mol, 1 equiv.) was charged to the activated acid. Rinse with acetonitrile (381 g). The temperature of the reaction mixture was adjusted to 50±5° C. and the mixture was agitated at 50±5° C. until the (R,Z)—N-(5-(N'-hydroxycarbamimidoyl)-2,3-dihydro-1H-inden-1-yl)-2-methyl-2H-tetrazole-5-carboxamide remaining was ≤2%. Once the reaction completion was confirmed, 1,8-diazabicyclo[5.4.0]undec-7-ene (DBU) (975.1 g, 6.41 mol, 2.0 equiv.) was added to the reaction mixture. The temperature of the mixture was adjusted to 70±5° C. and the mixture was agitated at 70±5° C. for until not more than 2% of the uncyclized intermediate remains. After confirmation of the reaction completion, the reaction mixture was quenched with water (28.96 kg). The mixture was slowly cooled to ambient temperature and held. The mixture was filtered and the product dried under vacuum. A total of 1,018 g (90% yield) of polymorphic Form I of (R)—N-(5-(5-isopropyl-1,2,4-oxadiazol-3-yl)-2,3-dihydro-1H-inden-1-yl)-2-methyl-2H-tetrazole-5-carboxamide was obtained as a light grey powder.

Figure 1E:
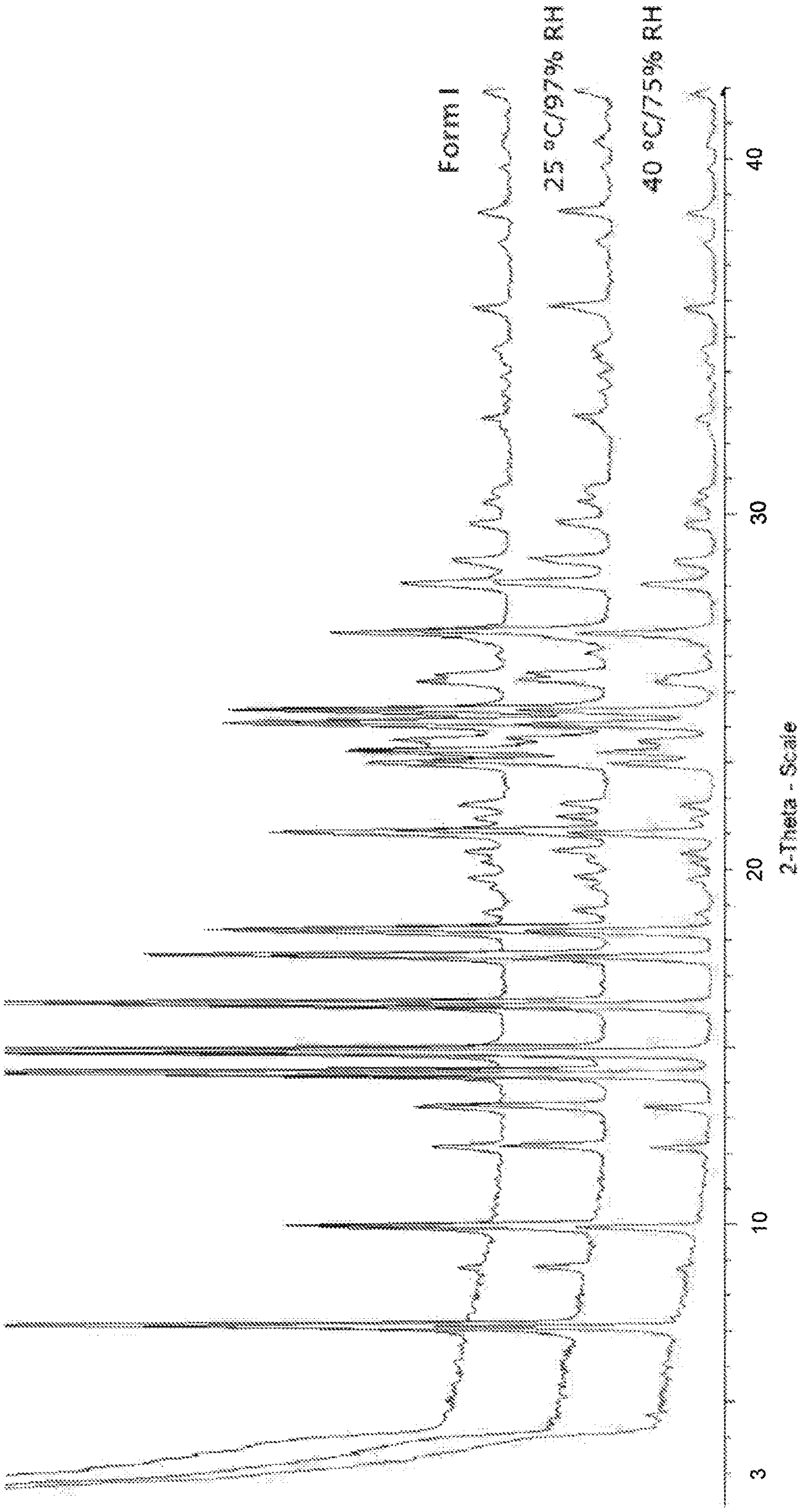
FIG. 1E shows XRPD patterns of polymorphic Form I of (R)—N-(5-(5-isopropyl-1,2,4-oxadiazol-3-yl)-2,3-dihydro-1H-inden-1-yl)-2-methyl-2H-tetrazole-5-carboxamide after storage for 7 days at 40° C./75% RH and 25° C./97% RH.

Polymorphic Form I of (R)—N-(5-(5-isopropyl-1,2,4-oxadiazol-3-yl)-2,3-dihydro-1H-inden-1-yl)-2-methyl-2H-tetrazole-5-carboxamide was analyzed by XRPD, DSC, TGA, and DVS. FIG. 1A shows an XRPD pattern of Form I. FIG. 1B shows DSC and TGA graphs of Form I. As shown in the DSC graph, an endotherm onset at about 153° C. was observed. As shown in the TGA graph, no weight loss prior to degradation, which starts at about 230° C., was observed. FIG. 1C shows a kinetic plot of DVS graph of Form I. FIG. 1D shows an isotherm plot of DVS graph of Form I. As shown in FIGS. 1C and 1D, a moisture uptake of 0.36% w/w over 0-90% relative humidity (RH) range as determined by DVS was observed. Chemical stability study of Form I was also performed. XRPD patterns were measured after storage of samples of Form I for 7 days at 40° C./75% RH and 25° C./97% RH. The results are shown in FIG. 1E. No significant changes in XRPD patterns after storage were observed.

Example 2. Preparation of Form II

Figure 2E:
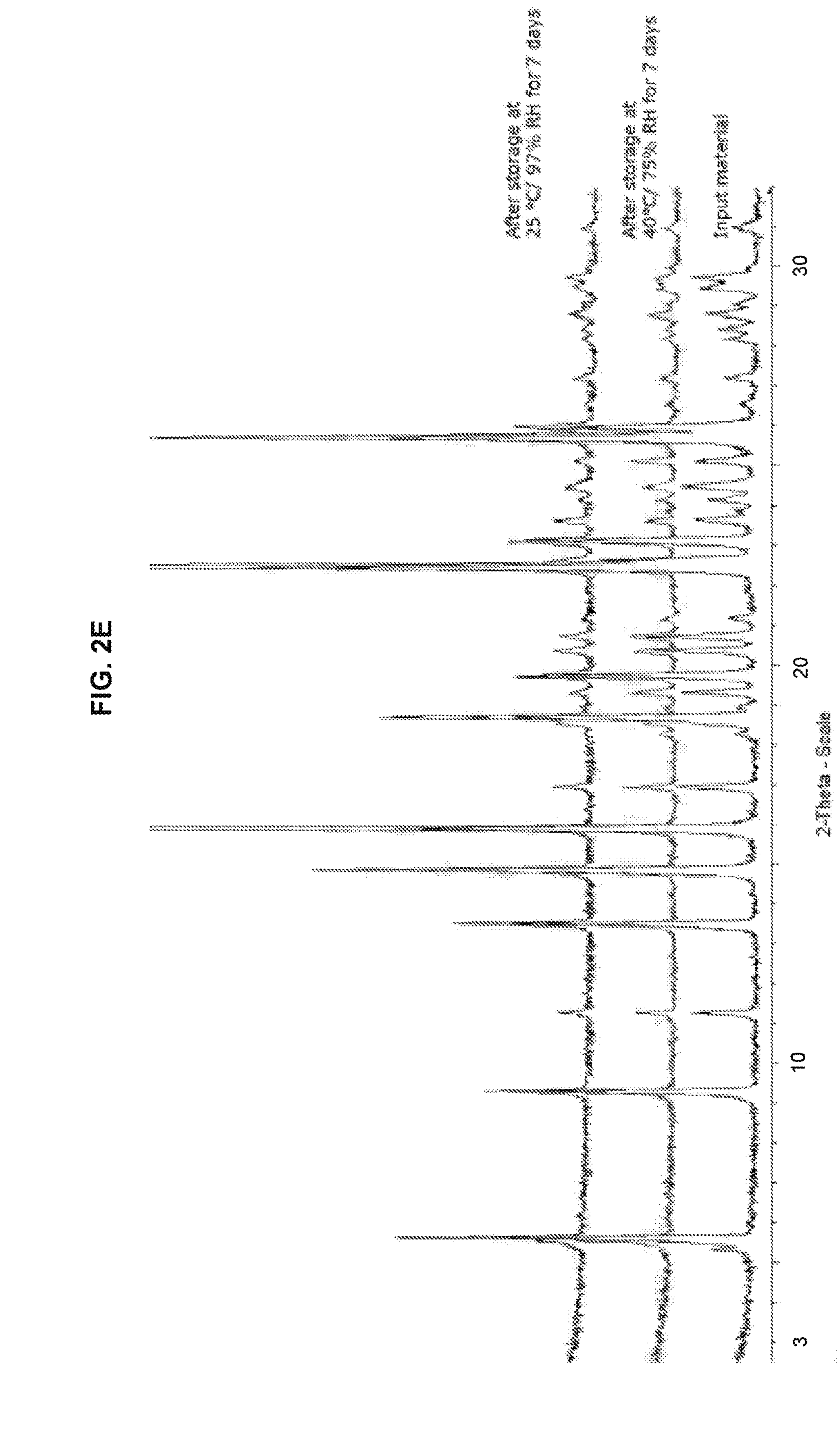
FIG. 2E shows XRPD patterns of polymorphic Form II of (R)—N-(5-(5-isopropyl-1,2,4-oxadiazol-3-yl)-2,3-dihydro-1H-inden-1-yl)-2-methyl-2H-tetrazole-5-carboxamide after storage for 7 days at 40° C./75% RH and 25° C./97% RH.

Polymorphic Form I of (R)—N-(5-(5-isopropyl-1,2,4-oxadiazol-3-yl)-2,3-dihydro-1H-inden-1-yl)-2-methyl-2H-tetrazole-5-carboxamide (500 mg) was suspended in n-propyl acetate (50 vol) and stirred at 50° C. After 10 minutes, a clear solution was obtained. The solvent was removed under reduced pressure (100 ml round-bottom flask). The solid obtained was analyzed by XRPD and determined as a mixture of Form I and Form II. The solid was suspended in n-propyl acetate (40 vol) and stirred at 50° C. After 10 minutes, a clear solution was obtained. The solvent was removed under reduced pressure in a larger flask (250 ml round-bottom flask). The resulting solid was analyzed by XRPD, DSC, TGA, and GVS and determined as Form II. FIG. 2A shows XRPD patterns of polymorphic Form I and Form II and their mixture thereof (from top to bottom: mixture of Form I and Form II, Form II, Form II, Form I). FIG. 2B shows DSC and TGA graphs of polymorphic Form II. As shown in the DSC graph (sample heated at 10° C./min), an endotherm onset at about 133° C., an exotherm onset at about 135° C., and an endotherm onset at about 152° C. were observed. As shown in the TGA graph, a weight loss of about 1.1% between about 83° C. and about 160° C. prior to degradation was observed. FIG. 2C shows a kinetic plot of DVS graph of Form II. FIG. 2D shows an isotherm plot of DVS graph of polymorphic Form II. As shown in FIGS. 2C and 2D, a moisture uptake of 0.24% w/w over 0-90% RH range as determined by DVS was observed. Chemical stability study of Form II was also performed. XRPD patterns were measured after storage of samples of Form II for 7 days at 40° C./75% RH and 25° C./97% RH. The results are shown in FIG. 2E. No significant changes in XRPD patterns after storage were observed.

Example 3. Polymorph Screening

Polymorph screen for (R)—N-(5-(5-isopropyl-1,2,4-oxadiazol-3-yl)-2,3-dihydro-1H-inden-1-yl)-2-methyl-2H-tetrazole-5-carboxamide was performed as detailed below.

Example 3.1. Solubility Assessment

Polymorphic Form I of (R)—N-(5-(5-isopropyl-1,2,4-oxadiazol-3-yl)-2,3-dihydro-1H-inden-1-yl)-2-methyl-2H-tetrazole-5-carboxamide (ca. 15 mg) was treated with increasing aliquots of solvent until dissolution was observed or a maximum of 100 vol had been added. The solubility assessment was performed at RT. Samples were shaken between each addition of solvent.

Solutions obtained were stored at 5° C. Solutions obtained from solvents with low freezing point (below 20° C.) were allowed to evaporate at ambient conditions. After 4 days, samples remaining as solutions were allowed to evaporate at ambient conditions.

Suspensions obtained were placed for maturation (RT/50° C., 4 hour cycles) for 4 days. An aliquot of each suspension was filtered through a Millipore plate and dried for 5 minutes prior to XRPD. Solids isolated from the screen were analyzed by XRPD and the results are shown below in Table 3. Form I was obtained from the majority of the solids isolated. Form II was isolated from evaporation of n-propyl acetate. A mixture of Form I and Form II was isolated from evaporation of MEK.

TABLE 3

| Solvent | Treatment | Observations after 4 days | Further treatment | XRPD |
|---|---|---|---|---|
| n-heptane | Maturation | Suspension | — | Form 1 |
| Diethyl ether | Maturation | Suspension | — | Form I |
| n-propyl acetate | Maturation | Solution | Evaporation at RT | Form II |
| Ethyl acetate | Storage at 5° C. | Solution | Evaporation at RT | Form 1 |
| iProAc | Storage at 5° C. | Solution | Evaporation at RT | Form I |
| MIBK | Storage at 5° C. | Solution | Evaporation at RT | Form I |
| IPA | Maturation | Solution | Evaporation at RT | Form I |
| MEK | Storage at 5° C. | Solution | Evaporation at RT | Mix of Forms I and II |
| 1-propanol | Maturation | Solution | Evaporation at RT | Form I |
| Acetone | Storage at 5° C. | Solution | Evaporation at RT | Form I |
| EtOH | Maturation | Solution | Evaporation at RT | Form I |
| DMSO | Evaporation | Solution | Evaporation at RT | Similar to Form I |
| $H_2O$ | Maturation | Suspension | — | Form I |
| TBME | Maturation | Suspension | — | Form I |
| 2-methyl-1-propanol | Maturation | Solution | Evaporation at RT | Form I |
| Cyclohexane | Maturation | Suspension | — | Form I |
| 1,4-dioxane | Evaporation | Solution | Evaporation at RT | Form I |
| Toluene | Maturation | Solution | Evaporation at RT | Form I |
| Chloroform | Storage at 5° C. | Solution | Evaporation at RT | Form I |
| 1,2-Dimethoxyethane | Storage at 5° C. | Solution | Evaporation at RT | Form I |
| THF | Storage at 5° C. | Solution | Evaporation at RT | Form I |
| DCM | Storage at 5° C. | Solution | Evaporation at RT | Form I |
| 2-methoxyethanol | Storage at 5° C. | Solution | Evaporation at RT | Form I |
| MeOH | Maturation | Solution | Evaporation at RT | Form I |
| DMF | Storage at 5° C. | Solution | Evaporation at RT | Form I |
| MeCN | Storage at 5° C. | Solution | Evaporation at RT | Form I |
| Ethyleneglycol | Maturation | Suspension | — | Form I |
| Nitromethane | Storage at 5° C. | Solution | Evaporation at RT | Form I |
| NMP | Storage at 5° C. | | Evaporation at RT | n/a-solution |
| THF:water (95:5 v/v) | Storage at 5° C. | Solution | Evaporation at RT | Form 1 |
| IPA:water (95:5 v/v) | Maturation | Solution | Evaporation at RT | Form I |
| EtOH:water (95:5 v/v) | Maturation | Solution | Evaporation at RT | Form I |
| Acetone: water (95:5 v/v) | Storage at 5° C. | Solution | Evaporation at RT | Form I |
| MeOH:water (95:5 v/v) | Maturation | Solution | Evaporation at RT | Form I |

Example 3.2. Isothermal Maturation

Polymorphic Form I of (R)—N-(5-(5-isopropyl-1,2,4-oxadiazol-3-yl)-2,3-dihydro-1H-inden-1-yl)-2-methyl-2H-tetrazole-5-carboxamide (ca. 2 g) was suspended in MeCN:$H_2O$ (90 vol) and stirred at 50° C. for 40 minutes. The clear solution was filtered and flash frozen in a dry ice/acetone bath and placed for lyophilisation. The solid isolated was analyzed by XRPD and determined to be poorly crystalline Form I.

Poorly crystalline Form I (ca. 15 mg) was dispensed into HPLC vials. Solvent was added (10 vol) and the samples were shaken/stirred at 50° C. After 6 days, suspensions were filtered through a Millipore filter plate and dried under suction for 30 minutes prior to XPRD analysis. As shown in Table 4 below, no new forms were identified, suggesting that Form I is the most stable form under the condition investigated.

TABLE 4

| Solvent | Initial observation | Observations after 6 days | Further Treatment | XRPD analysis |
|---|---|---|---|---|
| n-heptane | Suspension | Suspension | — | Form I |
| Diethyl ether | Suspension | Suspension | — | Form I |
| n-propyl acetate | Suspension | Suspension | — | Form I |
| Ethyl acetate | Suspension | Solution | Evaporation | Form I |
| iProAc | Suspension | Suspension | — | Form I |
| MIBK | Suspension | Suspension | — | Form I |
| IPA | Suspension | Suspension | — | Poorly crystalline Form I |
| MEK | Suspension | Solution | Evaporation | Form I |
| 1-propanol | Suspension | Suspension | — | Form I |
| Acetone | Suspension | Solution | Evaporation | Form I |
| EtOH | Suspension | Suspension | — | Form I |
| DMSO | Solution | Solution | Evaporation | Form I |
| $H_2O$ | Suspension | Suspension | — | Form I* |
| TBME | Suspension | Suspension | — | |
| 2-methyl-1-propanol | Suspension | Suspension | — | Form 1 |
| Cyclohexane | Suspension | Suspension | — | Poorly crystalline Form I |
| 1,4-dioxane | Solution | Solution | Evaporation | Form I |
| Toluene | Suspension | Suspension | — | Poorly crystalline Form I |
| Chloroform | Solution | Solution | Evaporation | Form I |
| 1,2-Dimethoxyethane | Suspension | Solution | Evaporation | Form I |
| THF | Solution | Solution | Evaporation | Form I |
| DCM | Solution | Solution | Evaporation | Form I |
| 2-methoxyethanol | Suspension | Suspension | — | Form I |
| MeOH | Suspension | Suspension | — | Form I |
| DMF | Suspension | Solution | Evaporation | Form I |
| MeCN | Suspension | Solution | Evaporation | Form I |
| Ethyleneglycol | Suspension | Suspension | — | Form I* |
| Nitromethane | Solution | Solution | Evaporation | Form 1 |
| NMP | Solution | Solution | Evaporation | n/a-solution |
| THF:water (95:5 v/v) | Solution | Solution | Evaporation | Form 1 |
| IPA:water (95:5 v/v) | Suspension | Suspension | — | Poorly crystalline Form I |
| EtOH:water (95:5 v/v) | Suspension | Suspension | — | Form I |
| Acetone:water (95:5 v/v) | Suspension | Solution | Evaporation | Form I |
| MeOH:water (95:5 v/v) | Suspension | Suspension | — | Form I |

Initially no diffraction (likely insufficient sample) therefore sample was re-analyzed

Example 3.3. Liquid Assisted Grinding

Polymorphic Form I of (R)—N-(5-(5-isopropyl-1,2,4-oxadiazol-3-yl)-2,3-dihydro-1H-inden-1-yl)-2-methyl-2H-tetrazole-5-carboxamide was dispensed into HPLC vials and two stainless steel grinding balls (3 mm diameter) added. Solvent was added (10 μl) and the samples were subjected to grinding on a Fritsch planetary mill (500 rpm, 2 hour duration). Solids obtained post grinding were analyzed by XRPD. As shown below in Table 5, Form I was obtained from all of the experiments. No new forms were identified, suggesting that Form I is the most stable form under the conditions investigated.

TABLE 5

| Solvent | XRPD | Solvent | XRPD |
|---|---|---|---|
| n-heptane | Form I | Toluene | Form I |
| Diethyl ether | Form I | Chloroform | Form I |
| n-propyl acetate | Form I | 1,2-Dimethoxyethane | Form I |
| Ethyl acetate | Form I | THF | Form I |
| iProAc | Form I | DCM | Form I |
| MIBK | Form I | 2-methoxyethanol | Form I |
| IPA | Form I | 2-methyl-1-propanol | Form I |
| MEK | Form I | DMF | Form I |
| 1-propanol | Form I | MeCN | Form I |
| Acetone | Form I | Ethyleneglycol | Form I |
| EtOH | Form I | Nitromethane | Form I |
| DMSO | Form I | NMP | Form I |
| HO | Form I | THF:water (95:5 v/v) | Form I |
| MeOH | Form I | IPA:water (95:5 v/v) | Form I |
| TBME | Form I | EtOH:water (95:5 v/v) | Form I |
| Cyclohexane | Form I | Acetone:water (95:5 v/v) | Form I |
| 1,4-dioxane | Form I | MeOH:water (95:5 v/v) | Form I |

Example 3.4. Temperature Cycling Maturation

Polymorphic Form I of (R)—N-(5-(5-isopropyl-1,2,4-oxadiazol-3-yl)-2,3-dihydro-1H-inden-1-yl)-2-methyl-2H-tetrazole-5-carboxamide (20 mg) was dispensed into HPLC vials. The selected solvent was added (5 vol) to each sample then placed for maturation (RT/50° C., cycled with 4 hours at each temperature). After 2 days, the samples were removed from the maturation chamber. Suspensions were filtered through a Millipore plate and dried under suction for 20 minutes prior to XRPD analysis. Solutions obtained were treated with increasing aliquots of anti-solvent until a suspension was obtained or maximum of 5 eq. had been added. Samples were shaken at 25° C. for 30 minutes. Suspensions obtained after shaking were filtered through a Millipore plate and dried under suction for 20 minutes prior to XRPD analysis. Solutions and samples containing a small amount of solid were shaken at 25° C. overnight with any solutions obtained allowed to evaporate at RT. Suspensions obtained were filtered through a Millipore plate and dried under suction for 20 minutes prior to XRPD analysis.

As shown below in Table 6, Form I was obtained from suspensions post maturation. Anti-solvent was added to the samples that remained as solutions. As shown below in Table 7, Form I was also obtained from the anti-solvent screen. No new forms were identified suggesting Form I is the most stable form under the conditions investigated.

TABLE 6

| Solvent | Observations after 2 days | Further treatment | XRPD analysis |
|---|---|---|---|
| n-heptane | Suspension | — | Form 1 |
| Diethyl ether | Suspension | — | Form 1 |
| n-propyl acetate | Suspension | — | Form I |
| Ethyl acetate | Suspension | — | Form I |
| iProAc | Suspension | — | Form I |
| MIBK | Suspension | — | Form I |
| IPA | Suspension | — | Form I |
| MEK | Suspension | — | Form I |
| 1-propanol | Suspension | — | Form I |
| Acetone | Solution | n/a* | Form I |
| EtOH | Suspension | — | Form I |
| DMSO | Solution | Treated with anti-solvent | Poorly crystalline Form I |
| $H_2O$ | Suspension | — | Poorly crystalline Form I |
| MeOH | Suspension | — | Form I |
| TBME | Suspension | — | Form I |
| Cyclohexane | Suspension | — | Form I |
| 1,4-dioxane | Solution | Treated with anti-solvent | Form I |
| Toluene | Suspension | — | Form I |
| Chloroform | Solution | Treated with anti-solvent | Form I |
| 1,2-Dimethoxyethane | Suspension | — | Form I |
| THF | Solution | Treated with anti-solvent | Form I |
| DCM | Solution | Treated with anti-solvent | Poorly crystalline Form I |
| 2-methoxyethanol | Suspension | — | Form I |
| 2-methyl-1-propanol | Suspension | — | Form I |
| DMF | Solution | Treated with anti-solvent | Form I |
| MeCN | Solution | Treated with anti-solvent | Form I |
| Ethyleneglycol | Suspension | — | Form I |
| Nitromethane | Solution | Treated with anti-solvent | Form I |
| NMP | Solution | Treated with anti-solvent | Form I |
| THF:water (95:5 v/v) | Solution | Treated with anti-solvent | Form I |
| IPA:water (95:5 v/v) | Suspension | — | Form I |
| EtOH:water (95:5 v/v) | Suspension | — | Form I |
| Acetone:water (95:5 v/v) | Solution | n/a* | Form I |
| MeOH:water (95:5 v/v) | Suspension | — | Form I |

TABLE 7

| Solvent | Anti-solvent | Treatment | Observations after shaking at 25° C. for 30 minutes | Observations after shaking at 25° C. overnight | XRPD analysis |
|---|---|---|---|---|---|
| DMSO | Water | Isothermal maturation at 25° C. | Suspension | — | Poorly crystalline Form I |
| 1,4-dioxane | Water | | Suspension | — | Form I |
| Chloroform | IPA | | Some solid | — | Form I |
| THF | IPA | | Suspension | Suspension | Form I |
| DCM | IPA | | Suspension | — | Poorly crystalline Form I |
| DMF | Water | | Suspension | — | Form I |
| MeCN | Water | | Suspension | — | Form I |
| Nitromethane | IPA | | Solution | Solution* | Form I |
| NMP | Water | | Suspension | | Form I |
| THF:water (95:5 v/v) | IPA | | Solution | Solution* | Form I |

Example 3.5. Anti-Solvent Experiments

Polymorphic Form I of (R)—N-(5-(5-isopropyl-1,2,4-oxadiazol-3-yl)-2,3-dihydro-1H-inden-1-yl)-2-methyl-2H-tetrazole-5-carboxamide (20 mg) was dispensed into HPLC vials and dissolved in the selected solvent (10 vol). Increasing aliquots of anti-solvent were added until a suspension was obtained or a maximum of 5 eq. had been added. Samples were shaken at 25° C. for 30 minutes.

Suspensions obtained were filtered through a Millipore plate and dried under suction for 20 minutes prior to XRPD analysis. Solutions and hazy solutions were shaken at 25° C. overnight. Suspensions obtained were filtered through a Millipore plate and dried under suction for 20 minutes prior to XRPD analysis. Solutions obtained post shaking were allowed to evaporate at ambient conditions.

Anti-solvent experiments were set up using IPA, heptane, water and TBME as anti-solvents. Observations from the experiments can be found below in Tables 8 and 9. Form I was obtained from most of the experiments. A potential mixture of Forms I and II was obtained from the experiment using chloroform and TBME.

TABLE 8

| Solvent | Anti-solvent | Treatment | Observation after shaking at 25° C. for 30 minutes | Observation after shaking at 25° C. overnight | Observation after evaporation | XRPD analysis |
|---|---|---|---|---|---|---|
| DMSO | IPA | Isothermal maturation at 25° C. | Solution | Solution | White solid | Form I |
| 1,4-dioxane | Heptane | | Suspension | n/a | n/a | Form I |
| THF | Heptane | | Suspension | n/a | n/a | Form I |
| DCM | Heptane | | Suspension | n/a | n/a | Form I |
| Nitromethane | IPA | | Solution | Solution | White needles | Form I |
| NMP | Heptane | Experiment stopped | n/a | n/a | n/a | n/a |
| THF:water (95:5 v/v) | Water | Isothermal maturation at 25° C. | Suspension | n/a | n/a | Form I |
| Chloroform | Heptane | | Suspension | n/a | n/a | Form I (poorly crystalline) |

TABLE 9

| Solvent | Anti-solvent | Treatment | Observations after 30 minutes | Observations after shaking at 25° C. overnight | Observation after evaporation | XRPD analysis |
|---|---|---|---|---|---|---|
| DMSO | TBME | Isothermal maturation at 25° C. | Solution | Solution | Paste | Form I |
| 1,4-dioxane | TBME | | | | White solid | Form I |
| THF | TBME | | | | White solid | Form I |
| DCM | TBME | | | | White needles | Form I |
| Nitromethane | TBME | | | | White solid | Form I |
| NMP | TBME | | | | Solution | n/a - solution |
| THF:water (95:5 v/v) | IPA | | | | White solid | Form I |
| Chloroform | TBME | | | | White solid | Poorly crystalline possibly mix of Forms I + II |

Example 4. Competitive Slurry Experiments Between Form I and Form II

Figure 3:
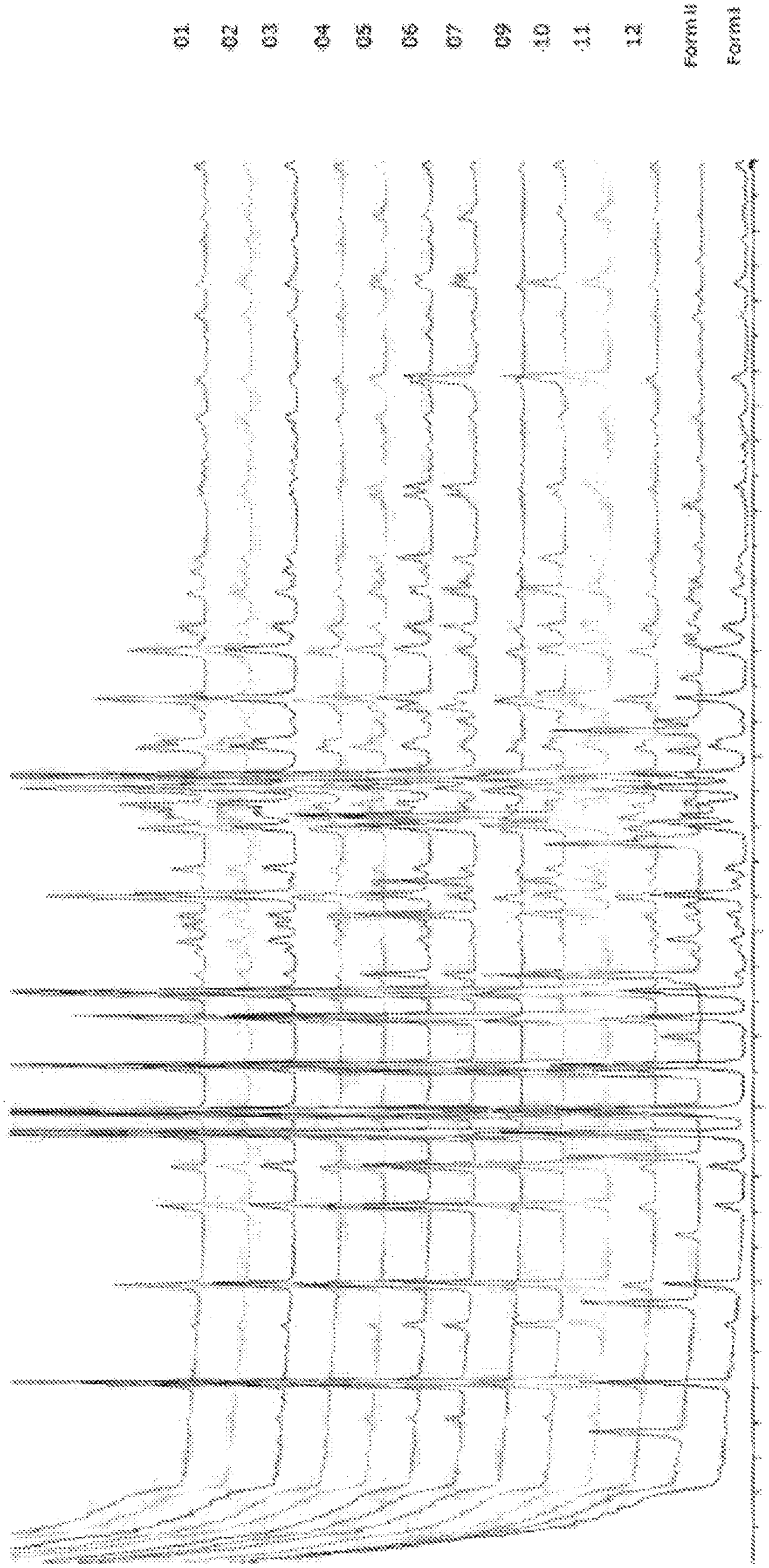
FIG. 3 shows the results of competitive slurry experiments between Form I and Form II.

Competitive slurry experiments between Form I and Form II in different solvents were conducted. Form I was suspended in the selected solvents at both 50° C. and 5° C. and stirred for a minimum of 1 hour before filtration to create a saturated solution. Form I (ca. 10 mg) and Form II (ca. 10 mg) were combined in a HPLC vial. Each sample was treated with 0.5 ml of the selected saturated solution. The samples were stirred at the selected temperature for 6 days. Solids obtained were filtered and dried under suction for a few minutes prior to characterization. Samples were slightly wet during XRPD analysis. The results of the experiments are shown in FIG. 3 and summarized in Table 10.

TABLE 10

| Sample ID | Solvent | Temperature/° C. | XRPD analysis |
|---|---|---|---|
| 01 | MeCN | 5 | Form 1 |
| 02 | n-propyl acetate | 5 | Form 1 |
| 03 | MEK | 5 | Form 1 |
| 04 | $H_2O$:MeCN (25:75) | 5 | Form 1 |
| 05 | $H_2O$:MeCN (75:25) | 5 | Form 1 |
| 06 | MeCN | 50 | Form I |
| 07 | n-propyl acetate | 50 | Form I |
| 08* | MEK | 50 | Solution |
| 09* | $H_2O$:MeCN (25:75) | 50 | Form I |
| 10 | $H_2O$:MeCN (75:25) | 50 | Form I |
| 11 | MEK | 50 | Form I |
| 12 | $H_2O$:MeCN (25:75) | 50 | Form I |

*Sample was also treated with neat solvent as there was not enough of the saturated solution. These experiments were reperformed as 11 and 12.

Example 5. Myofibril Assays

To evaluate the effect of (R)—N-(5-(5-isopropyl-1,2,4-oxadiazol-3-yl)-2,3-dihydro-1H-inden-1-yl)-2-methyl-2H-tetrazole-5-carboxamide on the ATPase activity of full-length cardiac myosin in the context of the native sarcomere, skinned myofibril assays were performed. Bovine cardiac myofibrils were obtained by homogenizing bovine cardiac left ventricular tissue in the presence of a detergent such as triton X-100. Such treatment removes membranes and a majority of the soluble cytoplasmic proteins but leaves intact the cardiac sarcomeric acto-myosin apparatus. Myofibril preparations retain the ability to hydrolyze ATP in a $Ca^{2+}$ regulated manner. ATPase activities of such myofibril preparations in the presence and absence of compounds were assayed at $Ca^{2+}$ concentrations activating to a defined fraction of the maximal rate (i.e., 25%, 75%). Small molecule agents were assessed for their ability to inhibit the steady-state ATPase activity of bovine cardiac myofibrils using pyruvate kinase and lactate dehydrogenase (PK/LDH)-coupled enzyme system. This assay regenerates myosin-produced ADP into ATP by oxidizing NADH, producing an absorbance change at 340 nm. Prior to testing small molecule agents, the bovine cardiac myofibrils were assessed for their calcium responsiveness and the calcium concentration that achieves either a 50% ($pCa_{50}$) or 75% ($pCa_{75}$) activation of the myofibril system was chosen as the final condition for assessing the inhibitory activity of the small molecule agents. All enzymatic activity was measured in a buffered solution containing 12 mM PIPES (piperazine-N, N'-bis(2-ethanesulfonic acid), 2 mM magnesium chloride at pH 6.8 (PM 12 buffer). Final assay conditions were 1 mg/mL of bovine cardiac myofibrils, 4 U/mL pyruvate kinase, 6 U/mL lactate dehydrogenase, 50 μM ATP, 0.1 mg/mL BSA (bovine serum albumin), 10 ppm antifoam, 1 mM DTT, 0.5 mM NADH, 1.5 mM PEP, 0.6 mM EGTA, and an amount of $CaCl_2$ sufficient to achieve either 50% or 75% activation of the myofibril ATPase activity. The $IC_{15}$ (CDMF75) for (R)—N-(5-(5-isopropyl-1,2,4-oxadiazol-3-yl)-2,3-dihydro-1H-inden-1-yl)-2-methyl-2H-tetrazole-5-carboxamide is 0.5 μM and $IC_{50}$ (CDMF75) for (R)—N-(5-(5-isopropyl-1,2,4-oxadiazol-3-yl)-2,3-dihydro-1H-inden-1-yl)-2-methyl-2H-tetrazole-5-carboxamide is 2.4 μM.

Example 6. Myocyte Assays

Adult male Sprague-Dawley rats were anesthetized and the hearts were quickly excised, rinsed and the ascending aorta was cannulated. Continuous retrograde perfusion was initiated on the hearts at a perfusion pressure of 60 cm $H_2O$. Hearts were first perfused with a nominally $Ca^{2+}$-free modified Krebs solution of the following composition: 113 mM NaCl, 4.7 mM KCl, 0.6 mM $KH_2PO_4$, 0.6 mM $Na_2HPO_4$, 1.2 mM $MgSO_4$, 12 mM $NaHCO_3$, 10 mM $KHCO_3$, 30 mM taurine, 5.5 mM glucose and 10 mM Hepes (all Sigma). This medium is not recirculated and is continually aerated with a 95% $O_2$/5% $CO_2$ mixture. After approximately 3 minutes the heart was perfused with a modified Krebs buffer supplemented with collagenase (Worthington) and 12.5 μM final calcium concentration. The heart was removed from the cannulae after the heart appeared blanched and soft in appearance. The atria and vessels were removed and the ventricles were gently dissected into smaller pieces with forceps. The tissue was homogenized by repeated pipette trituration and the collagenase reaction was stopped by 10% bovine calf serum (BCS), sedimentation and resuspension in perfusion buffer containing 5% BCS and 12.5 uM $CaCl_2$. Myocytes were made calcium tolerant by stepwise addition of a $CaCl_2$ solution to a final concentration of 1.2 mM. Cells were then washed and resuspended in Tyrode's buffer (137 mM NaCl, 3.7 mM KCl, 0.5 mM $MgCl_2$, 11 mM glucose, 4 mM Hepes, and 1.2 mM $CaCl_2$, pH 7.4). Cells were kept for 60 min at 37° C. prior to initiating experiments and used within 5 hrs of isolation. Preparations of cells were used only if cells first passed QC criteria by demonstrating a contractile response to standard (>150% of basal) and isoproterenol (ISO; >250% of basal) treatment. Additionally, only cells whose basal contractility was between 3 and 8% were used in subsequent experiments with compounds.

Aliquots of myocytes in Tyrode's buffer were placed in perfusion chambers (series 20 RC-27NE; Warner Instruments) complete with heating platforms. Myocytes were allowed to attach, the chambers were heated to 37° C., and the cells were perfused with 37° C. Tyrode's buffer. Myocytes were field stimulated at 1 Hz in with platinum electrodes (20% above threshold). Only cells that had clear striations and were quiescent prior to pacing were used for contractility experiments. To determine basal contractility, myocytes were imaged through a 40× objective. Using a variable frame rate (60-240 Hz) charge-coupled device camera, the images were digitized and displayed on a computer screen at a sampling speed of 240 Hz (IonOptix Milton, MA). Once cell contraction was stable over time, test compounds (0.01-15 μM) were perfused into the chambers on the myocytes for 5 minutes. Contractility of the myocytes and contraction and relaxation velocities were then recorded using edge detection.

Five or more individual myocytes were tested per compound from two or more different myocyte preparations. For each cell, twenty or more contractility transients at basal (defined as 1 min prior to compound infusion) and after compound addition (defined as 5 min after starting compound perfusion), were averaged and compared. These average transients were analyzed using the IonWizard software (IonOptix) to determine changes in diastolic length and fractional shortening. Fractional shortening was calculated as: ((resting length−length at peak contraction) divided by the resting length). The percent change in fractional shortening from baseline was calculated as: ((post-dose fractional shortening/basal fractional shortening)*100). The percent reduction in fractional shortening from baseline was calculated as: (100−percent change in fractional shortening from baseline). Maximum contraction and relaxation velocities (um/sec) was also determined. Results from individual cells are averaged and the SEM calculated. The effect of (R)—N-(5-(5-isopropyl-1,2,4-oxadiazol-3-yl)-2,3-dihydro-1H-inden-1-yl)-2-methyl-2H-tetrazole-5-carboxamide is provided below.

| Concentration (μM) | % FS (% reduction from baseline) ± SEM | # of cells tested |
|---|---|---|
| 5 | 67.8 ± −5.4 | 5 |

% FS = Average of each cell's (post baseline percent peak height/pre-baseline percent peak height) × 100

Example 7. Echocardiography Assessment of Acute Pharmacodynamic Effect in Rat Cardiac Contractility Assessment of in vivo cardiac function by echocardiography was performed in male Sprague Dawley rats under isoflurane (1-3%) anesthesia. 2-D M-mode images of the left ventricle were acquired in the parasternal long-axis view before, during, and after administration of compounds by continuous IV infusion or oral gavage. In vivo fractional shortening was determined by M-mode image analysis with the following calculation: ((End diastolic diameter−end systolic diameter)/end diastolic diameter×100). For continuous IV infusion experiments, three pre-dose baseline M-mode images were taken at 1 minute intervals prior to infusion of compound. Compounds were formulated in 50% Propylene Glycol (PG): 16% Captisol: 10% dimethylacetamide (DMA) and delivered via a jugular vein catheter at the rate of 1 mL/kg/h. During infusion, M-mode images were taken at 5 minute intervals. The infusion stopped when fractional shortening reached up to a 60% reduction from baseline. Blood samples were taken to determine the plasma concentration of the compounds. Data was reported as an estimated $IC_{50}$ value, which is the concentration at which fractional shortening is 50% of the pre-dose baseline contractility. The $IC_{50}$ value obtained for (R)—N-(5-(5-isopropyl-1,2,4-oxadiazol-3-yl)-2,3-dihydro-1H-inden-1-yl)-2-methyl-2H-tetrazole-5-carboxamide is 2.7±0.12 μM (Mean±S.D.).

For oral dosing studies, three pre-dose baseline M-Mode images were taken at 1 minute intervals prior to compound administration. (R)—N-(5-(5-isopropyl-1,2,4-oxadiazol-3-yl)-2,3-dihydro-1H-inden-1-yl)-2-methyl-2H-tetrazole-5-carboxamide was formulated in a 0.5% hydroxypropyl methylcellulose 2910 (HPMC 2910): 0.1% Tween 80 suspension and delivered as a single dose (5 mL/kg) by oral gavage. Rats were lightly anesthetized for M-Mode echocardiography measurements at select time points over a 24 hour period. Different dose levels were evaluated. The compound effect on cardiac fractional shortening at the highest dose evaluated is presented below as a percent reduction of baseline fractional shortening (=100%).

| Dose (mg/kg) | FS (% reduction from baseline) at 1-2 h post dose (Mean ± S.D.) | FS (% reduction from baseline) at 4 h post dose (Mean ± S.D.) |
|---|---|---|
| 6 | 40 ± 9 | 18 ± 11 |

Concurrent with echocardiography measurements, blood samples were taken to determine the corresponding compound plasma concentration. The estimated $IC_{50}$ and $IC_{10}$ values, which are the concentration at which fractional shortening is 50% and 10% of the pre-dose baseline contractility, respectively are 2.9 μM ($IC_{50}$) and 0.7 μM ($IC_{10}$).

All documents, including patents, patent application and publications cited herein, including all documents cited therein, tables, and drawings, are hereby expressly incorporated by reference in their entirety for all purposes.

While the foregoing written description of the compounds, uses, and methods described herein enables one of ordinary skill in the art to make and use the compounds, uses, and methods described herein, those of ordinary skill in the art will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

The invention claimed is:

1. A polymorph of (R)—N-(5-(5-isopropyl-1,2,4-oxadiazol-3-yl)-2,3-dihydro-1H-inden-1-yl)-2-methyl-2H-tetrazole-5-carboxamide of Form I or Form II, wherein Form I is characterized by having an XRPD pattern comprising peaks at angles 2-theta of 7.1±0.2, 14.2±0.2, 14.9±0.2, 16.2±0.2, and 18.3±0.2 degrees; and Form II is characterized by having an XRPD pattern comprising peaks at angles 2-theta of 14.9±0.2, 16.0±0.2, 18.8±0.2, 22.5±0.2, and 25.8±0.2 degrees.

2. The polymorph of Form I of claim 1, characterized by having an XRPD pattern comprising peaks at angles 2-theta of 7.1±0.2, 14.2±0.2, 14.9±0.2, 16.2±0.2, and 18.3±0.2 degrees.

3. The polymorph of Form I of claim 1, characterized by having an XRPD pattern comprising peaks at angles 2-theta of 7.1±0.2, 9.9±0.2, 14.2±0.2, 14.9±0.2, 16.2±0.2, 17.6±0.2, 18.3±0.2, 21.0±0.2, 24.1±0.2, and 24.5±0.2 degrees.

4. The polymorph of Form I of claim 1, characterized by having an endotherm onset at 153±2° C. as determined by DSC.

5. The polymorph of Form II of claim 1, characterized as having an XRPD pattern comprising peaks at angles 2-theta of 14.9±0.2, 16.0±0.2, 18.8±0.2, 22.5±0.2, and 25.8±0.2 degrees.

6. The polymorph of Form II of claim 1, characterized as having an XRPD pattern comprising peaks at angles 2-theta of 5.7±0.2, 9.4±0.2, 13.6±0.2, 14.9±0.2, 16.0±0.2, 18.8±0.2, 22.5±0.2, 22.7±0.2, 23.1±0.2, and 25.8±0.2 degrees.

7. The polymorph of Form II of claim 1, characterized as having an endotherm onset at 133±2° C. as determined by DSC, and/or an exotherm onset at 135±2° C. as determined by DSC, and/or an endotherm onset at 152±2° C. as determined by DSC.

8. A method of preparing a polymorph of Form I of claim 1, comprising:

(1) forming a mixture of (R)—N-(5-(5-isopropyl-1,2,4-oxadiazol-3-yl)-2,3-dihydro-1H-inden-1-yl)-2-methyl-2H-tetrazole-5-carboxamide and a solvent, wherein the solvent comprises acetonitrile; and (2) cooling or evaporating the mixture of step (1).

9. The method of claim 8, wherein step (1) comprises heating the mixture to 70±5° C.

10. The method of claim 8, wherein step (2) comprises cooling the mixture of step (1) to ambient temperature.

11. The method of claim 8, wherein an anti-solvent is added before step (2) is performed, wherein the anti-solvent is water.

12. A method of preparing a polymorph of Form II of claim 1, comprising:

(1) forming a mixture of polymorphic Form I of (R)—N-(5-(5-isopropyl-1,2,4-oxadiazol-3-yl)-2,3-dihydro-1H-inden-1-yl)-2-methyl-2H-tetrazole-5-carboxamide and a solvent, wherein the solvent comprises n-propyl acetate; and (2) removing the solvent.

* * * * *